United States Patent [19]

Klaus et al.

[11] 4,256,878

[45] Mar. 17, 1981

[54] POLYENE COMPOUNDS

[75] Inventors: Michael J. Klaus, Weil am Rhein, Fed. Rep. of Germany; Beverly A. Pawson, Montclair, N.J.

[73] Assignee: Hoffmann-La Roche Inc., Nutley, N.J.

[21] Appl. No.: 140,938

[22] Filed: Apr. 16, 1980

Related U.S. Application Data

[60] Division of Ser. No. 904,950, May 11, 1978, which is a division of Ser. No. 801,688, May 31, 1977, Pat. No. 4,116,975, which is a division of Ser. No. 733,507, Oct. 18, 1976, Pat. No. 4,061,656, which is a continuation-in-part of Ser. No. 632,029, Nov. 14, 1975, abandoned.

[51] Int. Cl.$^3$ .................. C07D 333/06; C07D 333/24
[52] U.S. Cl. ........................................ 542/412; 549/6; 542/405
[58] Field of Search ..................... 549/6; 542/405, 412

[56] References Cited

U.S. PATENT DOCUMENTS

| | | | |
|---|---|---|---|
| 3,666,765 | 5/1972 | Berijckere | 260/290 HL |
| 3,847,947 | 11/1974 | Epstein | 549/6 |
| 3,881,017 | 4/1975 | Vlattas | 424/275 |
| 3,970,670 | 7/1976 | Vlattas | 424/275 X |

FOREIGN PATENT DOCUMENTS 2422498 5/1974 Fed. Rep. of Germany .
2260801 6/1974 Fed. Rep. of Germany .

OTHER PUBLICATIONS

Acheson, et al., J. Chem. Soc., (1961), pp. 650–660.
Houben–Weyl, Methodender Organischen Chemie, 4th Ed., vol V/ld, p. 15, (1972).
Sporn, et al., Nature, vol. 253, pp. 47–50 (1975).
Yoshina, et al., J. Pharm. Soc., Japan, 88 (1968), pp. 398–404.
Venters, et al., C.A., 56, 10072a, 1962.

*Primary Examiner*—Joseph Paul Brust
*Attorney, Agent, or Firm*—Jon S. Saxe; Bernard S. Leon; George W. Johnston

[57] ABSTRACT

Novel-9-substituted or unsubstituted thienyl-3,7-dimethyl-nona-2,4,6,8-tetraene derivatives, useful as antitumor agents as well as processes for their preparation and novel intermediates are disclosed.

2 Claims, No Drawings

POLYENE COMPOUNDS

RELATED APPLICATIONS

This is a division, of application Ser. No. 904,950 filed May 11, 1978, which in turn is a division of U.S. patent application Ser. No. 801,688, filed May 31, 1977, now U.S. Pat. No. 4,116,975, which in turn is a division of Ser. No. 733,507 filed Oct. 18, 1976, now U.S. Pat. No. 4,061,656 which is in turn a continuation-in-part of U.S. patent application Ser. No. 632,029, filed Nov. 14, 1975, now abandoned.

SUMMARY OF THE INVENTION

In accordance with this invention, it has been discovered that compounds represented by the formula

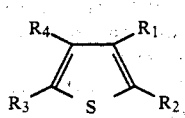

wherein one of $R_1$ or $R_2$ is

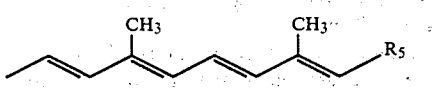

and the other of $R_1$ or $R_2$ and $R_3$ and $R_4$ are hydrogen, lower alkyl thio, lower alkoxy-lower alkyl, hydroxy methyl, halogen, lower alkyl, lower alkoxy, amino, carboxyl, mono(lower alkyl)amino, di(lower alkyl)amino, mono(lower alkyl) amino lower alkyl, di(lower alkyl)amino lower alkyl, hydroxy, lower alkenyl, lower alkenoxy, lower alkanoyl, lower alkanoyloxy, nitro, lower alkoxycarbonyl, lower alkanoylamino or a nitrogen containing heterocycle; and $R_5$ is formyl, hydroxymethyl, alkoxymethyl, alkanoyloxymethyl, carboxyl, alkoxycarbonyl, alkenoxycarbonyl, alkynoxycarbonyl, carbamoyl, mono(lower alkyl)carbamoyl, di(lower alkyl)carbamoyl, N-heterocyclylcarbonyl and aroyloxymethyl. and salts thereof are useful as antitumor agents.

DESCRIPTION OF THE INVENTION

The present invention pertains to compounds represented by the formula

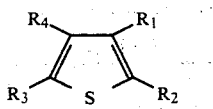 I wherein one of $R_1$ or $R_2$ is

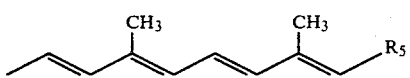

and the other of $R_1$ or $R_2$ and $R_3$ and $R_4$ are hydrogen, lower alkyl thio, lower alkoxy-lower alkyl, hydroxy methyl, halogen, lower alkyl, lower alkoxy, amino, carboxyl, mono(lower alkyl)amino, di(lower alkyl)amino, mono(lower alkyl) amino lower alkyl, di(lower alkyl)amino lower alkyl, hydroxy, lower alkenyl, lower alkenoxy, lower alkanoyl, lower alkanoyloxy, nitro, lower alkoxycarbonyl, lower alkanoylamido or a nitrogen containing heterocycle; and $R_5$ is formyl, hydroxymethyl, alkoxymethyl, alkanoyloxymethyl, carboxyl, alkoxycarbonyl, alkenoxycarbonyl, alkynoxycarbonyl, carbamoyl, mono(lower alkyl)carbamoyl, di(lower alkyl)carbamoyl, N-heterocyclylcarbonyl and aroyloxymethyl, and salts thereof.

As used herein "lower alkyl" means alkyl groups which contain up to 6 carbon atoms, e.g., methyl, ethyl, propyl, isopropyl or 2-methyl-propyl, "lower alkoxy" means alkoxy groups which contain up to 6 carbon atoms, e.g., methoxy, ethoxy or isopropoxy, "halogen" includes fluorine, chlorine, bromine and iodine with bromine and chlorine preferred, "lower alkenyl" means alkenyl groups which contain up to 6 carbon atoms, e.g., vinyl, allyl and butenyl, "lower alkoxy" means alkenoxy groups which contain up to 6 carbon atoms, e.g., vinyloxy and allyloxy, "lower alkanoyloxy" means alkanoyloxy groups which contain up to 6 carbon atoms, e.g., acetoxy, propionyloxy, butyryloxy and the like.

The alkanoyl portion of the lower alkanoylamido and lower alkanoyl groups are derived from lower alkanecarboxylic acids having up to 6 carbon atoms, e.g., acetic acid, propionic acid, pivalic acid, and the like. The term "aroyloxymethyl" means aroyloxymethyl groups wherein the aroyl portion is derived from an aromatic carboxylic acid residue containing from 7 to 11 carbon atoms, e.g., benzoic acid, toluic acid, xylylic acid and the like, preferred are benzoyloxymethyl and tolyloxymethyl.

The terms "alkoxymethyl" and "alkoxycarbonyl" include straight-chain or branched-chain alkoxy groups having up to 20 carbon atoms, e.g., methoxy, ethoxy, isopropoxy or cetyloxy. Preferred, however, are those alkoxy groups containing up to 6 carbon atoms. The said alkoxy groups can be unsubstituted or substituted by functional groups, for example, by nitrogen-containing groups such as by substituted or alkyl-substituted amino or morpholino groups, or by a piperidyl or pyridyl group. The terms "alkenoxycarbonyl" and "alkynoxycarbonyl" include alkenoxy and alkynoxy groups having up to 6 carbon atoms, e.g., allyloxy or propargyloxy. The alkanoyloxy groups present in the alkanoyloxymethyl groups are derived from alkanecarboxylic acids containing from 1 to 20 carbon atoms, e.g., acetic acid, propionic acid, pivalic acid, palmitic acid or stearic acid, however, the preferred group of alkanecarboxylic acids are the lower alkanecarboxylic acids which contain from 1 to 6 carbon atoms. The carbamoyl group within the scope of this invention can be monosubstituted or disubstituted by straight-chain or branched-chain lower alkyl groups, e.g., methyl, ethyl or isopropyl. Examples of such substituted carbamoyl groups are the methylcarbamoyl, dimethylcarbamoyl and diethylcarbamoyl groups. The terms "N-heterocyclyl" and "nitrogen containing heterocycle" include 5-membered or 6-membered heterocyclic groups which, in addition to nitrogen, may contain a second nitrogen, oxygen or sulphur. Of the heterocyclic rings piperidino, morpholino, thiomorpholino and pyrrolidino are preferred.

Preferred compounds within the scope of formula I are represented by the formula

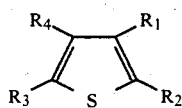

wherein one of $R_1$ or $R_2$ is

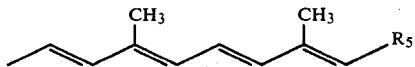

and the other of $R_1$ or $R_2$ and $R_3$ and $R_4$ are hydrogen, lower alkyl or halogen and $R_5$ is lower alkoxycarbonyl, carboxyl or mono(lower alkyl)carbamoyl, and salt thereof.

Examples of polyene compounds within the scope of this invention are all trans-3,7-dimethyl-9-(2,4,5-trimethyl-3-thienyl)-2,4,6,8-nonatetraenoic acid ethyl ester;

all trans-3,7-dimethyl-9-(2,4,5-trimethyl-3-thienyl)-2,4,6,8-nonatetraenoic acid;

all trans-N-ethyl-3,7-dimethyl-9-(2,4,5-trimethyl-3-thienyl)-2,4,6,8-nonatetraenamide;

all trans-3,7-dimethyl-9-(3,4,5-trimethyl-2-thienyl)-2,4,6,8-nonatetraenoic acid ethyl ester;

all trans-3,7-dimethyl-9-(3-methyl-2-thienyl)-2,4,6,8-nonatetraenoic acid ethyl ester;

all trans-3,7-dimethyl-9-(5-methyl-2-thienyl)-2,4,6,8-nonatetraenoic acid ethyl ester;

all trans-3,7-dimethyl-9-(2,5-dimethyl-3-thienyl)-2,4,6,8-nonatetraenoic acid ethyl ester;

all trans-3,7-dimethyl-9-(3,4,5-tribromo-2-thienyl)-2,4,6,8-nonatetraenoic acid ethyl ester;

all trans-3,7-dimethyl-9-(3,4-dibromo-5-methyl-2-thienyl)-2,4,6,8-nonatetraenoic acid ethyl ester;

all trans-3,7-dimethyl-9-(2,4-dimethyl-5-chloro-3-thienyl)-2,4,6,8-nonatetraenoic acid ethyl ester;

all trans-3,7-dimethyl-9-(2,4-dimethyl-5-methoxy-3-thienyl)-2,4,6,8-nonatetraenoic acid ethyl ester;

all trans-3,7-dimethyl-9-(2,4-dichloro-5-methyl-3-thienyl)-2,4,6,8-nonatetraenoic acid ethyl ester;

all trans-3,7-dimethyl-9-(2,4-diethyl-5-methyl-3-thienyl)-2,4,6,8-nonatetraenoic acid ethyl ester;

all trans-3,7-dimethyl-9-(2,4-dimethyl-5-methoxymethyl-3-thienyl)-2,4,6,8-nonatetraenoic acid ethyl ester;

all trans-3,7-dimethyl-9-(2,4-dimethyl-5-dimethylamino-3-thienyl)-2,4,6,8-nonatetraenoic acid ethyl ester;

all trans-3,7-dimethyl-9-(2,5-dichloro-3-thienyl)-2,4,6,8-nonatetraenoic acid ethyl ester;

all trans-3,7-dimethyl-9-(2,5-dichloro-4-methyl-3-thienyl)-2,4,6,8-nonatetraenoic acid ethyl ester;

all trans-3,7-dimethyl-9-(2,4-dimethyl-5-acetyl-3-thienyl)-2,4,6,8-nonatetraenoic acid ethyl ester;

all trans-3,7-dimethyl-9-[2,4-dimethyl-5-(1-methoxyethyl)-3-thienyl]-2,4,6,8-nonatetraenoic acid ethyl ester;

all trans-3,7-dimethyl-9-(5-bromo-2-thienyl)-2,4,6,8-nonatetraenoic acid ethyl ester;

all trans-3,7-dimethyl-9-(2,4,5-trimethyl-3-thienyl)-2,4,6,8-nonatetraen-1-ol;

2,4,6-trans-8-cis-3,7-dimethyl-9-(3,4,5-tribromo-2-thienyl)-2,4,6,8-nonatetraenoic acid ethyl ester;

all trans-3,7-dimethyl-9-(3,4-dibromo-2-thienyl)-2,4,6,8-nonatetraenoic acid ethyl ester;

all trans-3,7-dimethyl-9-(2,4,5-trimethyl-3-thienyl)-1-methoxy-2,4,6,8-nonatetraene;

all trans-3,7-dimethyl-9-(2,4-diethoxycarbonyl-5-acetylamino-3-thienyl)-2,4,6,8-nonatetraenoic acid ethyl ester;

all trans-3,7-dimethyl-9-(3-methyl-5-methoxy-2-thienyl)-2,4,6,8-nonatetraenoic ethyl ester;

all trans-3,7-dimethyl-9-(2,4,5-trimethyl-3-thienyl)-2,4,6,8-nonatetraen-1-al;

all trans-3,7-dimethyl-9-(2,4,5-trimethyl-3-thienyl)-2,4,6,8-nonatetraenamide;

all trans-3,7-dimethyl-9-(2,4-dimethyl-3-thienyl)-2,4,6,8-nonatetraenoic acid ethyl ester;

all trans-3,7-dimethyl-9-[2,4-dimethyl-5-(methylthio)-3-thienyl]-2,4,6,8-nonatetraenoic acid ethyl ester;

2,4,6-trans-8-cis-3,7-dimethyl-9-(3,4-dibromo-5-methyl-2-thienyl)-2,4,6,8-nonatetraenoic acid ethyl ester;

2,4,6-trans-8-cis-3,7-dimethyl-9-(3-thienyl)-2,4,6,8-nonatraenoic acid ethyl ester;

all trans-3,7-dimethyl-9-(3-thienyl)-2,4,6,8-nonatetraenoic acid ethyl ester.

The polyene compounds of this invention represented by formula I are pharmacodynamically valuable. They are effective in regressing the growth of tumors such as papillomas.

The toxicity of the compounds of this invention is slight. For example, when all trans-3,7-dimethyl-9-(2,4,5-trimethyl-3-thienyl)-2,4,6,8-nonatetraenoic acid ethyl ester is administered intraperitoneally to mice weighing 30 g. in a daily dosage of 100 mg./kg., then no indication of a hypervitaminosis-A becomes evident after 14 days (total of 10 administration days).

The first indications of hypervitaminois-A in mice appears at a daily dosage of 200 mg./kg. after 14 days (total of 10 administration days). This manifests itself in a weight decrease and a moderate hair loss and slight flaking of the skin.

The tumor-inhibiting activity of the compounds represented by formula I is significant. In the papilloma test, tumors induced with dimethylbenzanthracene and croton oil regress. The diameter of the papillomas within two weeks after the intraperitoneal administration of all trans-3,7-dimethyl-9-(2,4,5-trimethyl-3-thienyl)-2,4,6,8-nonatetraenoic acid ethyl ester decreases by 79% at a dosage of 400 mg./kg./week and by 60% at a dosage of 100 mg./kg./week.

The following Table illustrates the activity and toxicity of the compounds of this invention.

TABLE

| Example | Hypervitaminosis effective dose mg/kg/day | Papilloma Effect Dose mg/kg/wk | ±% regression |
|---|---|---|---|
| 3 | 100–200 (borderline) | 400 | −69, −79, −59 |
|   | 400 | 200 | −66, −83, −50 |
|   |   | 100 | −60, −57, −22 |
|   |   | 50 | −42, −22 |
| 4 | 200 |   |   |
| 5 | >200 | 400 | −28 |
|   |   | 200 | −25 |
|   |   | 100 | −14 |
| 8 | 100 | 400 | −47 |
|   | 50 (borderline) | 400 po | −35 |
| 12 | >200 | 400 | −18 |
| 14 | 100 | 400 | −64 |
|   | 50 (borderline) |   |   |
| 37 | 50 | 200 | −69 |
| 51 | >400 | 400 | −58, −34 |
| 54 (cis trans) | 200 | 400 | −11 |
| 55 |   | 400 | −7 |
| 57 (cis trans) | >200 | 400 | −17 |

TABLE-continued

| Example | Hypervitaminosis effective dose mg/kg/day | Papilloma Effect Dose mg/kg/wk | ±% regression |
|---|---|---|---|
| 57 (all trans) | >200 | 400 | −26 |
| 61 | 100 | 200 | −34 |
| 65 | 50 | 100 | −29 |
| 69 | >200 | 400 | −23 (toxic) |
| 73 | 200 | 400 | −43 |
| 104 | 100 | 200 | −39 |

The compounds represented by formula I can be used as medicaments in the form of pharmaceutical preparations which contain them in association with a compatible carrier material.

Pharmaceutical preparations for systemic administration can be prepared, for example, by adding a compound represented by formula I as the active ingredient to pharmaceutically acceptable, non-toxic, inert, solid or liquid carriers which are usual in such preparations. The pharmaceutical preparations can be administered topically, enterally or parenterally. Suitable preparations for enteral administration are, for example, tablets, capsules, dragees, syrups, suspension, solutions and suppositories. Suitable pharmaceutical preparations for parenteral administration are infusion solutions.

The dosages in which the compounds are administered can be varied according to the mode and route of administration and according to the requirements of the patient. For example, the compounds can be administered in amounts of from 5 mg. to 200 mg. daily in one or more dosages. Capsules containing about 10 mg. to about 100 mg. of the active compound are a preferred form of administration.

The pharmaceutical preparations can contain in addition to the active compounds of this invention, pharmaceutically acceptable inert or pharmacodynamically active additives. Tablets or granules, for example, can contain a series of pharmaceutically acceptable binders, fillers, carrier materials or diluents. Liquid preparations can, for example, take the form of sterile water-miscible solutions. Capsules can contain a pharmaceutically acceptable filler or thickener. Furthermore, pharmaceutically acceptable flavor-improving additives and pharmaceutically acceptable substances commonly used as preservatives, stabilizers, moisture-retainers or emulsifiers, salts for varying the osmotic pressure, buffers and other pharmaceutically acceptable additives can also be present in the pharmaceutical preparations.

The aforementioned pharmaceutically acceptable carrier materials and diluents are well known to the pharmaceutical compounding art and can be inorganic or inorganic substances such as water, gelatin, lactose, starch, magnesium stearate, talc, gum arabic, polyalkyleneglycols and the like. It is, of course, a prerequisite that all adjuvants used in the preparation of the pharmaceutical preparations are non-toxic and pharmaceutically acceptable.

For topical administration, the compounds of this invention are expediently made up in the form of salves, tinctures, creams, solutions, lotions, sprays, suspensions and the like. Ointments, creams and solutions are preferred. These pharmaceutical preparations for topical administration can be prepared by mixing a compound of this invention as the active ingredient with pharmaceutically acceptable non-toxic, inert, solid or liquid carriers which are customary in such preparations and which are suitable for topical administration.

Compositions for topical administration for use according to this invention contain on a weight basis the following amount of active compound: about 0.01% to about 0.3%, preferably about 0.02% to about 0.1%, in solutions and about 0.05% to about 5%, preferably about 0.1%, to about 2%, in ointments or creams.

A conventional pharmaceutically acceptable antioxidant, e.g., tocopherol, N-methyl-γ-tocopheramine, butylated hydroxyanisole or butylated hydroxytoluene can also be incorporated into the pharmaceutical preparations containing the compounds of this invention.

The compounds represented by formula I can be utilized as salts with pharmaceutically acceptable acids and bases. The salts can be prepared by reacting a carboxylic acid of formula I by conventional means with a base, e.g., alkali metal hydroxides, NaOH or KOH or an amine of formula I with an organic or inorganic acid, e.g., hydrohalic acid, HCl or HBr or benzoic, acetic, citric or lactic acids.

The compounds represented by formula I can be produced by reacting a compound represented by the formula

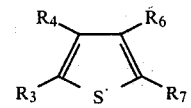

II wherein one of $R_6$ or $R_7$ is

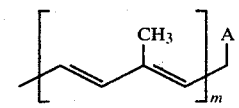

and the other of $R_6$ or $R_7$ and $R_3$ and $R_4$ are hydrogen, lower alkyl thio, lower alkoxy-lower alkyl, hydroxy methyl, halogen, lower alkyl, lower alkoxy, amino, carboxyl, mono(lower alkyl)amino, di(lower alkyl)amino, mono(lower alkyl)amino lower alkyl, di(lower alkyl)amino lower alkyl, hydroxy, lower alkenyl, lower alkenoxy, lower alkanoyl, lower alkanoyloxy, nitro, lower alkoxycarbonyl, lower alkanoylamido or a nitrogen containing heterocycle; m is 0 or 1, A is oxo, —P[X]$_3$+y− or

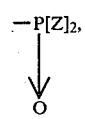

X is aryl, Z is lower alkoxy and y is an anion of an organic acid or an inorganic acid,
with a compound represented by the formula

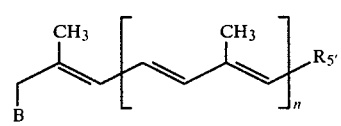

III wherein, B is oxo when A from the compound of formula II is —P[X]$_3$+y− or

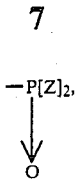

or when said A is oxo, B is —P[X]$_3$+y⁻ or

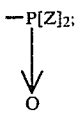

n is 0 or 1 and X, y and Z are the same as in formula II; when B is

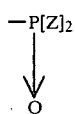

or —P[X]$_3$+y⁻, R$_5$ is formyl, carboxyl, lower alkoxycarbonyl, lower alkenyloxycarbonyl, lower alkynyloxycarbonyl, di(lower alkyl)carbamoyl or N-heterocyclylcarbonyl; when B is oxo, R$_5$, is carboxyl, lower alkoxymethyl, lower alkanoyloxy methyl, lower alkoxycarbonyl, lower alkenyloxycarbonyl, lower alkynyloxycarbonyl or N-heterocyclylcarbonyl.

In formulas II and III, the sum of m and n is always one.

The "aryl" group denoted by X includes all generally known aryl groups, preferred are mononuclear aryl groups such as phenyl, lower alkyl-substituted phenyl or lower alkoxy-substituted phenyl, e.g., xylyl, mesityl and p-methoxyphenyl. The inorganic acid anions denoted by y are preferably the chloride, bromide, iodide, and hydrosulfate. The preferred organic acid anion denoted by y is tosyloxy.

The products of the reaction between compounds of formula II and formula III which contain a carboxyl at R$_5$, can be esterified or amidated at the carboxyl. When R$_5$, is carboxyl or an ester, the reaction product can be reduced at R$_5$, to form a hydroxymethyl. The hydroxymethyl at R$_5$, can be esterified or etherified. The resulting alcohol ester can be saponified if desired. In cases where R$_5$, is a free hydroxymethyl or an ester thereof, such groups can be oxidized to form the corresponding compound where R$_5$, is formyl or carboxyl.

The compounds represented by formula II are, in part, novel and are within the scope of this invention. Certain novel compounds within formula II are those represented by the formula

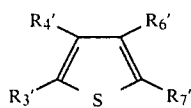

IIa wherein one of R'$_6$ or R'$_7$ is

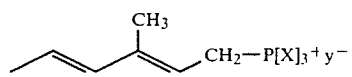

and the other of R'$_6$ or R'$_7$ and R'$_3$ and R'$_4$ are hydrogen, lower alkyl thio, lower alkoxy-lower alkyl, hydroxy methyl, halogen, lower alkyl, lower alkoxy, amino, carboxyl, mono(lower alkyl)amino, di(lower alkyl)amino, mono(lower alkyl)amino lower alkyl, di(lower alkyl)amino lower alkyl, hydroxy, lower alkenyl, lower alkenoxy, lower alkanol, lower alkanoyloxy, nitro, lower alkoxycarbonyl, lower alkanoylamido or a nitrogen containing heterocycle; X is aryl and y is an anion of an organic acid or an inorganic acid and the formula

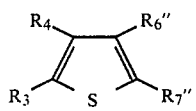

IIb wherein one of R''$_6$ or R''$_7$ is

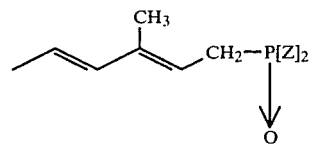

and the other of R'$_6$ or R''$_7$ and R$_3$ and R$_3$ and R$_4$ are hydrogen, lower alkyl thio, lower alkoxy-lower alkyl, hydroxymethyl, halogen, lower alkyl, lower alkoxy, amino, carboxyl mono(lower alkyl)amino, di(lower alkyl)amino, mono(lower alkyl)amino lower alkyl, di(lower alkyl)amino lower alkyl, hydroxy, lower alkenyl, lower alkenoxy, lower alkanoyl, lower alkanoyloxy, nitro, lower alkoxycarbonyl, lower alkanoylamido or a nitrogen containing heterocycle; and Z is lower alkoxy.

In addition some of the compounds wherein one of R'$_6$ or R'$_7$ is —CH$_2$—P[X]$_3$+y⁻ or one of R''$_6$ or R''$_7$ is

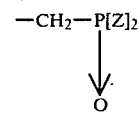

are novel.

The compounds of formula II wherein R$_6$ or R$_7$ is —CH$_2$—P[X]$_3$+y⁻ or

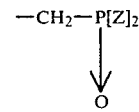

can be prepared by treating the corresponding substituted thiophene with formaldehyde in the presence of a hydrohalic acid, e.g., concentrated hydrochloric acid, in a solvent such as glacial acetic acid if desired, to form the halide. The halide is then reacted in a conventional manner with a triaryl phosphine in a solvent, preferably triphenyl phosphine in toluene or benzene, or with a trialkyl phosphite, e.g., triethyl phosphite.

The compounds of formula II wherein R$_6$ or R$_7$ is

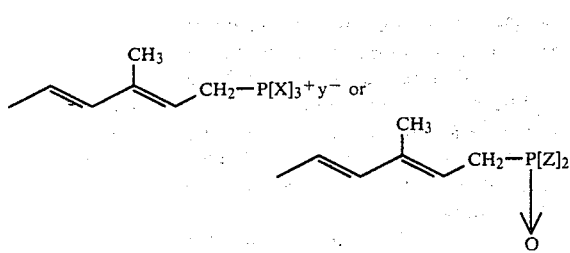

can be prepared by first formylating the corresponding thiophene, for example, in the presence of a Lewis acid. As the formylating agent there can be used an orthoformic acid ester, formyl chloride, dimethylformamide and N-methyl formanilide. Especially suitable Lewis acids are the halides of zinc, aluminum, titanium, tin and iron, e.g., zinc chloride, aluminum trichloride, titanium tetrachloride, tin tetrachloride and iron trichloride as well as the halides of inorganic and organic acids such as phosphorus oxychloride and methane sulfochloride.

If the formylating agent is present in excess, the formylation may be carried out without the addition of a further solvent. In general, however, the formylation should be carried out in an inert solvent, e.g., nitrobenzene or chlorinated hydrocarbons such as methylene chloride. The formulation can be carried out at a temperature between 0° C. and the boiling point of the mixture.

A resulting substituted thiophenecarboxaldehyde can subsequently be chain-lengthened in a conventional manner by condensation with acetone in the cold, i.e., about 0° C.-30° C. in the presence of alkali, e.g., dilute aqueous sodium hydroxide to give a substituted thienyl-but-3-en-2-one which can be converted into the corresponding substituted thienyl-3-methyl-3-hydroxy-penta-4-en-1-yne by conventional means, e.g., by means of a Grignard reaction by the addition of acetylene. The resulting acetylenic carbinol can subsequently by partially hydrogenated in a conventional manner using a partially deactivated noble metal catalyst, e.g., Lindlar catalyst. The resulting tertiary ethylenic carbinol can alternatively by synthesized by addition of a vinyl magnesium halide to the substituted thienyl-but-3-en-2-one.

The thus formed tertiary ethylenic carbinol can subsequently be converted, under allyl rearrangement, into the desired phosphonium salt.

The compounds of formula II wherein $R_6$ or $R_7$ is

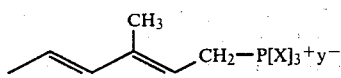

can be prepared by treatment of the tertiary ethylenic carbinol with a triaryl phosphine, preferably triphenyl phosphine, in the presence of a hydrohalide such as hydrogen chloride or hydrogen bromide in a solvent, e.g., benzene. The tertiary ethylenic carbinol can, moreover, be halogenated to give result in the compound of formula II where m is 1 and A is halide. This halide can be reacted with a trialkyl phosphite, e.g., triethyl phosphite to yield a corresponding phosphonate of formula II wherein $R_6$ or $R_7$ is

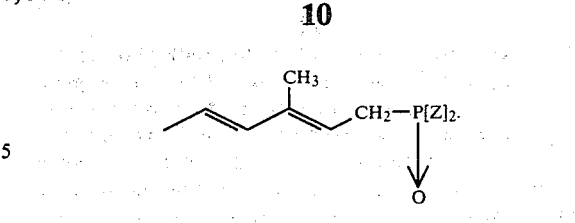

Compounds of formula II wherein m is 0 and A is oxo can be prepared, for example, by formylating a substituted thiophene as described above to form the corresponding thiophene carboxaldehyde.

Compounds of formula II wherein m is 1 and A is oxo can be prepared, for example, by submitting a substituted thienyl-but-3-en-2-one, described above, to a Wittig reaction with ethoxycarbonyl methylene-triphenylphosphorane or with diethyl-phosphonoacetic acid ethyl ester. The resulting substituted thienyl-3-methyl-penta-2,4-dien-1-oic acid ethyl ester is subsequently reduced in the cold with a mixed metal hydride, e.g., lithium aluminum hydride, in an organic solvent such as diethyl ether or tetrahydrofuran to yield a substituted thienyl-3-methyl-penta-2,4-dien-1-ol. The dienol is then oxidized with an oxidizing agent such as manganese dioxide in an organic solvent, e.g., acetone or methylene chloride, at a temperature between 0° C. and the boiling point of the mixture to give the corresponding substituted thienyl-3-methyl-penta-2,4-dien-1-al.

The compounds represented by formula III are prepared as follows.

Compounds of formula III where n is zero and B is a triarylphosphonium group or a dialkoxyphosphinyl group can be readily prepared by reacting an optionally esterified 3-halomethyl-crotonic acid or an etherified 3-halo-methylcrotyl alcohol with a triaryl phosphine in a solvent, preferably with triphenyl phosphine in toluene or benzene, or with a trialkyl phosphite, such as triethyl phosphite.

Compounds of formula III where n is 1 and B is a triarylphosphonium group or a dialkoxyphosphinyl group can be prepared, for example, by reducing the formyl group of the corresponding aldehyde in which n is 1 to the hydroxymethyl group using a metal hydride such as sodium borohydride in an alkanol, e.g., ethanol or isopropanol.

The resulting alcohol can be halogenated using a conventional halogenating agent, e.g., phosphorus oxychloride and the resulting 8-halo-3,7-dimethyl-octa-2,4,6-triene-1-carboxylic acid ester, a halide of formula III in which n is 1 and B is halogen or a derivative thereof can be reacted either with a triaryl phosphine in a solvent, preferably triphenyl phosphine in toluene or benzene, to give a phosphonium salt or with a trialkyl phosphite, preferably triethyl phosphite, to give the corresponding phosphonate.

Compounds of formula III where n is zero and B is an oxo group can be prepared, for example, by oxidatively cleaving an optionally esterified tartaric acid; for example, using lead tetraacetate at room temperature in an organic solvent such as benzene. The resulting glyoxalic acid derivative is subsequently condensed in a conventional manner, e.g., conveniently in the presence of an amine, with propionaldehyde at an elevated temperature, e.g., at a temperature between 60° C. and 110° C. with water cleavage to yield the corresponding 3-formyl-crotonic acid derivative.

Compounds of formula III where n is 1 and B is an oxo group can be prepared, for example, by reacting 4,4-dimethoxy-3-methyl-but-1-en-3-ol with phosgene in the cold, preferably at −10° C. to −20° C., in the presence of a tertiary amine such as pyridine and condensing the resulting 2-formyl-4-chloro-but-2-ene, a halide of formula III where B is halogen and n is 0, under conditions of a Wittig reaction with an optionally esterified 3-formyl-crotonic acid or to an optionally esterified or etherified 3-formyl-crotyl alcohol to yield the corresponding aldehyde of formula III.

The reaction of aldehydes of formula II with phosphonium salts or phosphoranes of formula III or aldehydes of formula III with phosphonium salts or phosphoranes of formula II to produce compounds of formula I can be carried out by, for example, either the Wittig or Horner techniques.

According to the Wittig procedure, the reaction components are reacted with one another in the presence of an acid binding agent, for example, in the presence of an alkali metal alcoholate such as sodium methylate or in the presence of an optionally alkyl-substituted alkylene oxide, preferably in the presence of ethylene oxide or 1,2-butylene oxide. If desired a solvent, e.g., a chlorinated hydrocarbon such as methylene chloride or dimethylformamide can be used. The reaction is carried out at a temperature between room temperature and the boiling point of the reaction mixture.

According to the Horner procedure, the reaction components are reacted with one another with the aid of a base and preferably in the presence of an inert organic solvent; for example, with the aid of sodium hydride in benzene, toluene, dimethylformamide, tetrahydrofuran, dioxan or 1,2-dimethoxyethane or with the aid of an alkali metal alcoholate in an alkanol, e.g., sodium methylate in methanol at a temperature between 0° C. and the boiling point of the reaction mixture.

For convenience, the reactions described hereinbefore can, in some cases, be carried out without isolating the phosphonium salt or phosphonate from the medium in which it is prepared.

A carboxylic acid of formula I can be converted by conventional means, e.g., by treatment with thionyl chloride, preferably in pyridine, into an acid chloride which can be converted by treatment with ammonia or with an amine into an amide and by reaction with an alkanol into an ester.

A carboxylic acid ester of formula I can be hydrolyzed by conventional means, e.g., by treatment with an alkali, preferably aqueous-alcoholic sodium hydroxide or potassium hydroxide, at a temperature between room temperature and the boiling point of the mixture and then amidated either via an acid halide or as described hereinafter.

A carboxylic acid ester of formula I can be converted directly into the corresponding amide, for example, by treatment with lithium amide. The lithium amide is advantageously treated with the ester at room temperature.

A carboxylic acid or a carboxylic acid ester of formula I can be reduced by conventional means to give the corresponding alcohol of formula I. The reduction is advantageously carried out using a metal hydride or alkyl metal hydride in an inert solvent. The preferred hydrides are the mixed metal hydrides such as lithium aluminum hydride or bis[methoxyethylenoxy]-sodium aluminum hydride. Suitable solvents are, inter alia, ether, tetrahydrofuran or dioxan when lithium aluminum hydride is used and ether, hexane, benzene or toluene when diisobutyl aluminum hydride or bis[methoxyethylenoxy]-sodium aluminum hydride is used.

An alcohol of formula I can be etherified with an alkyl halide, e.g., ethyl iodide, in the presence of a base, preferably sodium hydride, in an organic solvent such as dioxan, tetrahydrofuran, 1,2-dimethoxyethane, dimethylformamide at a temperature between 0° C. and room temperature.

An alcohol of formula I can also be esterified by treatment with an alkanoyl halide or anhydride, expediently in the presence of a base, e.g., pyridine or triethylamine at a temperature between room temperature and the boiling point of the mixture.

An alcohol ester can be saponified by conventional means, for example, by the process previously described in connection with the hydrolysis of a carboxylic acid ester.

An alcohol of formula I or an ester thereof can be oxidized by conventional means to give the corresponding acid of formula I. The oxidation is advantageously carried out with silver (I) oxide and alkali in water or in an organic water-miscible solvent at a temperature between room temperature and the boiling point of the mixture.

An amine of formula I forms addition salts with inorganic and organic acids. Examples of such salts are those formed with hydrohalic acids, preferably hydrochloric or hydrobromic acid, with other mineral acids, e.g., sulphuric acid and with organic carboxylic acids, e.g., benzoic acid, acetic acid, citric acid or lactic acid.

A carboxylic acid of formula I forms salts with bases, preferably with alkali metal hydroxides, e.g., sodium hydroxide or potassium hydroxide.

The compounds of formula I can occur as cis/trans mixtures which, if desired, can be separated into the cis and trans components or isomerised to the all-trans compounds by conventional means.

The following examples illustrate the invention. In the examples, the ether utilized was diethyl ether. In the examples concentrated hydrochloric acid denotes an aqueous solution containing about 37% by weight hydrochloric acid. The term 35% formaldehyde which appears in the examples indicates an aqueous solution containing 35% formaldehyde.

The sodium hydride (50–60%) utilized in the examples refers to a mineral oil suspension containing 30 to 60% by weight sodium hydride.

EXAMPLE 1

2,4,5-Trimethyl-3-chloromethyl-thiophene 24.6 G. of 2,3,5-trimethyl-thiophene, 14.8 g. of freshly distilled chloromethyl methyl ether and 52 g. of glacial acetic acid were combined in a glass pressure bottle and stirred at room temperature for 4½ hours. The resulting reaction mixture was poured into ice water, stirred for 10 min. and extracted with benzene. The combined benzene extracts were washed twice with saturated sodium chloride solution, dried over sodium sulfate, filtered and evaporated. The resulting 2,4,5-trimethyl-3-chloromethyl-thiophene was used for the next step without any further purification.

EXAMPLE 2

(2,4,5-Trimethyl-3-thenyl)triphenyl phosphonium chloride 33.2 G. of 2,4,5-trimethyl-3-chloromethyl-thiophene and 55.0 g. of triphenyl phosphine were dissolved in 200 ml. of benzene. The resulting mixture was refluxed overnight under argon and then cooled to room temperature. The precipitated white phosphonium salt which formed was collected by filtration, washed several times with cold benzene and dried at 80° C. under high vacuum to yield (2,4,5-trimethyl-3-thenyl)triphenyl phosphonium chloride, m.p. 236°–237° C.

EXAMPLE 3

All trans-3,7-dimethyl-9-(2,4,5-trimethyl-3-thienyl)-2,4,6,8-nonatetraenoic acid ethyl ester 10 G. of (2,4,5-trimethyl-3-thenyl)triphenyl phosphonium chloride was suspended in 200 ml. of butylene oxide then 5.2 g. of 3-methyl-7-formyl-octa-2,4,6-trienoic acid ethyl ester were added. The resulting mixture was refluxed under argon with stirring until a clear solution resulted. After heating for another 15 min. the solvent was evaporated. The oily residue was diluted with about 300 ml. of a methanol/water mixture (ratio 6:4) and extracted four times with hexane. The combined hexane solutions were washed once with methanol/water (6:4) and twice with pure water, dried with sodium sulfate, filtered and evaporated. The resulting crude product was purified by column chromatography (hexane/5% ether) and recrystallized from hexane/ether (4:1) to give all trans-3,7-dimethyl-9-(2,4,5-trimethyl-3-thienyl)-2,4,6,8-nonatetraenoic acid ethyl ester, m.p. 88°–89° C.

EXAMPLE 4

All trans-3,7-dimethyl-9-(2,4,5-trimethyl-3-thienyl)-2,4,6,8-nonatetraenoic acid 4.35 G. of all trans-3,7-dimethyl-9-(2,4,5-trimethyl-3-thienyl)-2,4,6,8-nonatetraenoic acid ethyl ester was dissolved in 30 ml. of ethanol and a solution of 3 g. of potassium hydroxide in 6 ml. of water and 6 ml. of ethanol was added. The resulting reaction mixture was stirred under argon for 2.5 hours at 50° C. After cooling, the resulting solution was poured on ice water, acidified with 3 N sulfuric acid and extracted several times with methylene chloride. The organic phase was washed twice with water, dried over sodium sulfate, filtered and evaporated. The resulting crude material was recrystallized from ethyl acetate to yield all trans-3,7-dimethyl-9-(2,4,5-trimethyl-3-thienyl)-2,4,6,8-nonatetraenoic acid, m.p. 208°–212° C.

EXAMPLE 5

All trans-N-ethyl-3,7-dimethyl-9-(2,4,5-trimethyl-3-thienyl)-2,4,6,8-nonatetraenamide 1.78 G. of all trans-3,7-dimethyl-9-(2,4,5-trimethyl-3-thienyl)-2,4,6,8-nonatetraenoic acid were suspended in 20 ml. of benzene. 563 Mg. of phosphorus trichloride were dropped into the suspension at room temperature. After stirring at 30° C. for about 3 hours, the acid was dissolved and a red solution of the acid chloride resulted. The red solution was dropped into a mixture of 800 mg. of ethylamine and 20 ml. of methylene chloride at 5°–10° C. After stirring for one hour at room temperature, the resulting reaction mixture was diluted with methylene chloride, poured into a saturated sodium chloride solution and extracted three times with methylene chloride. The combined organic phases were washed once with saturated sodium chloride solution, dried over sodium sulfate, filtered and evaporated. Recrystallization from ethyl acetate gave all trans-N-ethyl-3,7-dimethyl-9-(2,4,5-trimethyl-3-thienyl)-2,4,6,8-nonatetraenamide, m.p. 184°–187° C.

EXAMPLE 6

2-Hydroxymethyl-3,4,5-trimethyl-thiophene 1.9 G. of 3,4,5-trimethyl-2-thiophenecarboxaldehyde were dissolved in 20 ml. of ethanol. The resulting solution was cooled to 0°–5° C. and 125 mg. of sodium borohydride were added in small portions. The resulting reaction mixture was stirred at room temperature for 3 hours, poured into ice water, extracted with ethyl acetate, dried with sodium sulfate, filtered and evaporated. The resulting crystalline 2-hydroxymethyl-3,4,5-trimethyl-thiophene had m.p. 45°–48° C.

EXAMPLE 7

(3,4,5-Trimethyl-2-thenyl)triphenyl phosphonium bromide 2.2 G. of 2-hydroxymethyl-3,4,5-trimethyl-thiophene were dissolved in 25 ml. of acetonitrile and 4.6 g. of triphenylphosphonium bromide were added. The resulting reaction mixture was heated to 50° C. for 3 hours. After evaporation of the solvent, the residue which formed was diluted with ethyl acetate, heated briefly and filtered. The crystalline (3,4,5-trimethyl-2-thenyl)-triphenyl phosphonium bromide obtained was dried at 50° C. under high vacuum and had m.p. 208°–215° C.

EXAMPLE 8

All trans-3,7-dimethyl-9-(3,4,5-trimethyl-2-thienyl)-2,4,6,8-nonatetraenoic acid ethyl ester 3.2 G. of (3,4,5-trimethyl-2-thenyl)triphenyl phosphonium bromide were suspended in 80 ml. of butylene oxide and 1.5 g. of 3-methyl-7-formyl-octa-2,4,6-trienoic acid ethyl ester were added. The resulting mixture was refluxed under argon for one hour after which the solvent was evaporated. The residue which formed was diluted with a mixture of methanol/water (6:4) and extracted four times with hexane. The combined hexane solutions were washed once with methanol/water (6:4) and twice with pure water, dried with sodium sulfate, filtered and evaporated. The resulting crude product was purified by column chromatography on silica gel and elution with hexane/5% ether. Recrystallization of the all trans-3,7-dimethyl-9-(3,4,5-trimethyl-2-thienyl)-2,4,6,8-nonatetraenoic acid ethyl ester so obtained from hexane/1% ethyl acetate gave yellow crystals, m.p. 96°–98° C.

EXAMPLE 9

(3-methyl-2-thenyl)triphenyl phosphonium bromide

2-Hydroxymethyl-3-methyl-thiophene (4.5 g.) was dissolved in 90 ml. of acetonitrile and 12.3 g. of triphenylphosphonium bromide were added. The reaction mixture was heated to 70° C. for 3 hours. After cooling the resulting precipitate was filtered off, washed with benzene and dried at 80° C. under high vacuum. The resulting (3-methyl-2-thenyl)triphenylphosphonium bromide has a m.p. 266°–269° C.

EXAMPLE 10

All trans-3,7-dimethyl-9-(3-methyl-2-thienyl)-2,4,6,8-nonatetraenoic acid ethyl ester Sodium hydride (1.16 g. of a 50% suspension in mineral oil) was washed three times with pentane, dried and suspended in 50 ml. of dimethylformamide. At 0° C. a suspension of 7.5 g. of (3-methyl-2-thenyl)triphenylphosphonium bromide in 25 ml. of dimethylformamide was dropped in. After stirring for 15 minutes, a solution of 3.74 g. of 3-methyl-7-formyl-octa-2,4,6-trienoic acid ethyl ester in 40 ml. of dimethylformamide was dropped in. After stirring for 2.5 hours at room temperature the reaction mixture was poured into a methanol/water mixture (ratio 6:4) and extracted several times with hexane. The combined organic phases were washed once with methanol/water (6:4), dried over sodium sulfate, filtered and evaporated. The crude product was purified by recrystallization from hexane to give all-trans-3,7-dimethyl-9-(3-methyl-2-thienyl)-2,4,6,8-nonatetraenoic acid ethyl ester, m.p. 86°–87° C.

EXAMPLE 11

(5-methyl-2-thenyl)triphenylphosphonium bromide

2-Hydroxymethyl-5-methyl-thiophene (4.6 g.) was dissolved in 100 ml. of acetonitrile and 12.2 g. of triphenylphosphonium bromide were added. The reaction mixture was heated to 75° C. for 2.5 hours. After cooling the resulting precipitate was filtered off, washed with benzene and dried at 80° C. under high vacuum. The resulting (5-methyl-2-thenyl)triphenylphosphonium bromide has a m.p. 262°–266° C.

EXAMPLE 12

All-trans-3,7-dimethyl-9-(5-methyl-2-thienyl)-2,4,6,8-nonatetraenoic acid ethyl ester Sodium hydride (1.45 g. of a 50% suspension in mineral oil) was washed three times with pentane, dried and suspended in 75 ml. of dimethylformamide. At 0° C. a suspension of 10.3 g of (5-methyl-2-thenyl)triphenylphosphonium bromide in 50 ml. of dimethylformamide was dropped in. After stirring for 15 minutes, a solution of 6.25 g. of 3-methyl-7-formyl-octa-2,4,6-trienoic acid ethyl ester in 50 ml. of dimethylformamide was dropped in. After stirring for 1 hour at room temperature the reaction mixture was poured into a methanol/water mixture (ratio 6:4) and extracted several times with hexane. The combined organic phases were washed once with methanol/water (6:4), dried over sodium sulfate, filtered and evaporated. The crude product was purified by recrystallization from hexane to give all-trans-3,7-dimethyl-9-(5-methyl-2-thienyl)-2,4,6,8-nonatetraenoic acid ethyl ester, m.p. 92°–93° C.

EXAMPLE 13

(2,5-dimethyl-3-thenyl)triphenylphosphonium chloride

Triphenylphosphine (11.8 g.) and 7.0 g. of 2,5-dimethyl-3-chloromethylthiophene were dissolved in 100 ml. of toluene. The mixture was refluxed overnight under argon, cooled to room temperature and the precipitated white phosphonium salt was collected by filtration, washed several times with cold benzene and dried at 80° C. under high vacuum. The resulting (2,5-dimethyl-3-thenyl)-triphenylphosphonium chloride has a m.p. 246°–250° C.

EXAMPLE 14

All-trans-3,7-dimethyl-9-(2,5-dimethyl-3-thienyl)-2,4,6,8-nonatetraenoic acid ethyl ester (2,5-Dimethyl-3-thenyl)triphenylphosphonium chloride (7.0 g.) were suspended in 200 ml. of butylene oxide and 3.4 g. of 3-methyl-7-formyl-octa-2,4,6-trienoic acid ethyl ester were added. The mixture was refluxed under argon for 5.5 hrs. The resulting solution was poured into 500 ml. of a methanol/water mixture (ratio 6:4), extracted four times with hexane, washed with methanol/water, dried over sodium sulfate, filtered and evaporated. The crude product was purified by recrystallization from hexane to give all trans-3,7-dimethyl-9-(2,5-dimethyl-3-thienyl)-2,4,6,8-nonatetraenoic acid ethyl ester, m.p. 119°–121° C.

EXAMPLE 15

(3,4,5-tribromo-2-thenyl)triphenylphosphonium chloride

Triphenylphosphine (9.0 g.) and 10.4 g. of 3,4,5-tribromo-2-chloromethylthiophene were dissolved in 200 ml. of toluene. The mixture was refluxed overnight under argon, cooled to room temperature and the precipitated phosphonium salt was collected by filtration, washed several times with cold benzene and dried at 80° C. under high vacuum. The resulting (3,4,5-tribromo-2-thenyl)triphenylphosphonium chloride has a m.p. 248°–249° C.

EXAMPLE 16

All trans-3,7-dimethyl-9-(3,4,5-tribromo-2-thienyl)-2,4,6,8-nonatetraenoic acid ethyl ester Following the procedure of Example 10 (3,4,5-tribromo-2-thenyl)triphenyl phosphonium chloride is condensed with 7-formyl-3-methyl-octa-2,4,6-trienoic acid ethyl ester to form all trans-3,7-dimethyl-9-(3,4,5-tribromo-2-thienyl)-2,4,6,8-nonatetraenoic acid ethyl ester, which is recrystallized from hexane/5% ethyl acetate, m.p. 84°–86° C.

EXAMPLE 17

2-chloromethyl-3,4-dibromo-5-methyl-thiophene

A solution of 11.7 g. of 2-methyl-3,4-dibromo-thiophene in 30 ml. of acetic acid was added to 60 ml. of concentrated hydrochloric acid. After dropping in 4.1 g. of a 37% aqueous solution of formaldehyde the mixture was heated to 70° C. for one hour. The reaction mixture was cooled, diluted with water and extracted with ether. The combined organic phases were washed with water, sodium bicarbonate and water, dried over sodium sulfate, filtered and evaporated to give 2-chloromethyl-3,4-dibromo-5-methyl-thiophene.

EXAMPLE 18

(3,4-dibromo-5-methyl-2-thenyl)triphenyl phosphonium chloride (3,4-Dibromo-5-methyl-2-thenyl)triphenyl phosphonium chloride can be prepared in a manner analogous to that described in Example 13 by reaction of 2-chloromethyl-3,4-dibromo-5-methyl-thiophene with triphenyl phosphine, m.p. 215°–216° C.

EXAMPLE 19

All trans-3,7-dimethyl-9-(3,4-dibromo-5-methyl-2-thienyl)-2,4,6,8-nonatetraenoic acid ethyl ester By the procedure of Example 14 (3,4-dibromo-5-methyl-2-thenyl)triphenyl phosphonium chloride is condensed with 7-formyl-3-methyl-octa-2,4,6-trienoic acid ethyl ester to form all trans-3,7-dimethyl-9-(3,4-dibromo-5-methyl-2-thenyl)-2,4,6,8-nonatetraenoic acid ethyl ester, which is recrystallized from hexane/ethyl acetate (1:1), m.p. 150°–153° C.

EXAMPLE 20

Glyoxalic acid butyl ester 1775 g. of lead tetraacetate (90%) are gradually introduced within 30 minutes at 25°–30° C. into a solution of 1000 g. of L(+)-tartaric acid dibutyl ester in 3850 ml. of benzene. The reaction mixture is subsequently stirred for 1 hour at room temperature. The sediment is filtered off and extracted with 500 ml. of benzene. The benzene extract is evaporated under reduced pressure. The remaining glyoxalic acid butyl ester boils, after rectification, at 50°–65° C./12 mm Hg.

EXAMPLE 21

3-formyl-crotonic acid butyl ester

836 G. of the obtained glyoxalic acid butyl ester are introduced into 376 g. of propionaldehyde. The mixture is treated dropwise at 60° C. with 40.8 g. of di-n-butylamine. In so doing, the reaction temperature should not rise higher than 105° C. The reaction mixture is then stirred for 2 hours at 116°–111° C., cooled and taken up in ether. The diethyl ether extract is washed successively with 500 ml. of 1 N sulphuric acid, 700 ml. of water, 1000 ml. of 5% of weight aqueous sodium bicarbonate solution and subsequently with 1000 ml. of water, dried over sodium sulphate and evaporated under reduced pressure. The remaining 3-formyl-crotonic acid butyl ester boils, after rectification, at 93°–105° C./14 mm. Hg.; $n_D^{25}=1$.

EXAMPLE 22

4,4-dimethoxy-3-methyl-but-1-yn-3-ol

After the addition of a slight amount of iron (III) nitrate, 2700 ml. of liquid ammonia are treated portion-wise with stirring and cooling with 169.5 g. of potassium. As soon as the initially blue coloration has disappeared, i.e., after about 30–45 minutes, acetylene gas in a stream of 3 l/min. is led in until the dark coloration of the reaction mixture becomes lighter. Then, the gas stream is reduced to 2 l/min. and the mixture treated dropwise with a solution of 500 g. of methylglyoxal-dimethylacetal in 425 ml. of abs. diethyl ether. The introduction of acetylene is continued for 1 hour with stirring. The reaction mixture is subsequently treated portion-wise with 425 g. of ammonium chloride, gradually warmed to 30° C. within 12 hours with evaporation of the ammonia and extracted with 1600 ml. of diethyl ether. The ether extract is dried over sodium sulfate and evaporated under reduced pressure. The remaining 4,4-dimethoxy-3-methyl-but-1-yn-3-ol boils, after rectification, at 33° C./0.03 mm Hg; $n_D^{25}=1.4480$.

EXAMPLE 23

4,4-dimethoxy-3-methyl-but-1-en-3-ol

198 G. of 4,4-dimethoxy-3-methyl-but-1-yn-3-ol are dissolved in 960 ml. of high-boiling petroleum ether and, after the addition of 19.35% palladium catalyst and 19.3 g. of quinoline, hydrogenated under normal conditions. After the uptake of 33.5 l. of hydrogen, the hydrogenation is stopped. The catalyst is filtered off. The filtrate is evaporated under reduced pressure. The remaining 4,4-dimethoxy-3-methyl-but-1-en-3-ol boils, after rectification, at 70°–72° C./18 mm Hg.

EXAMPLE 24

2-formyl-4-chloro-but-2-ene

195 Ml. of phosgene are led into 1570 ml. of carbon tetrachloride at −10° C. After the addition of 213 g. of pyridine, the solution is treated dropwise at a temperature of −10° to −20° C. with 327 4,4-dimethoxy-3-methyl-but-1-en-3-ol. The reaction mixture is slowly warmed to 25° C. with stirring, stirred for a further 3 hours at room temperature, cooled to 15° C. and treated with 895 ml. of water. The aqueous phase is separated and rejected. The organic phase is treated, after standing for 12 hours in the cold, with 448 ml. of 5% by weight aqueous sulphuric acid, stirred for 5 hours, then washed with water, dried over sodium sulphate and evaporated under reduced pressure. The remaining 2-formyl-4-chloro-but-2-ene boils, after rectification, at 37°–40° C./1.8 mm Hg; $n_D^{25}=1.4895$.

EXAMPLE 25

2-formyl-but-2-ene-4-triphenyl-phosphonium chloride 165.7 G. of 2-formyl-4-chloro-but-2-ene are dissolved in 840 ml. of benzene and treated with 367 g. of triphenyl phosphine. The reaction mixture is heated to boiling under reflux conditions for 12 hours in a nitrogen atmosphere, then cooled to 20° C. The precipitated 2-formyl-but-2-ene-4-triphenyl-phosphonium chloride melts, after washing with benzene and drying, at 250°–252° C.

EXAMPLE 26

7-formyl-3-methyl-octa-2,4,6-trien-1-oic acid butyl ester 212.6 G. of 2-formyl-but-2-ene-4-triphenyl-phosphonium chloride and 95 g. of 3-formyl-crotonic acid butyl ester are introduced into 1100 ml. of butanol and treated at 5° C. with a solution of 57 g. of triethylamine in 60 ml. of butanol. The reaction mixture is subsequently stirred for 6 hours at 25° C., then cooled and introduced into water and thoroughly extracted with hexane. The hexane phase is washed first repeatedly with methanol/water (6:4 parts by volume), then with water, dried over sodium sulphate and filtered. The filtrate is isomerized for 12 hours by shaking with iodine. The iodine is removed by the addition of sodium thiosulphate. The filtrate is washed again with water, dried and evaporated under reduced pressure. The remaining 7-formyl-3-methyl-octa-2,4,6-trien-1-oic acid butyl ester boils, after rectification, at 102°–105° C./0.09 mm Hg.

EXAMPLE 27

8-diethoxy-phosphono-3,7-dimethyl-octa-2,4,6-trien-1-oic acid ethyl ester 3.03 G. of 8-bromo-3,7-dimethyl-octa-2,4,6-trien-1-oic acid ethyl ester are heated with 1.66 g. of triethylphosphite slowly to 125° C. The surpus bromo ester is distilled off. The residue is cooled and poured into ice and extracted with diethyl ether and an aqueous solution of sodium-hydrogen carbonate, dried and evaporated under reduced pressure. The remaining 8-diethoxy-phosphono-3,7-dimethyl-octa-2,4,6-trien-1-oic acid ethyl ester is immediately treated, as described in Example 28, with 2,4,5-trimethyl-3-thiophenecarboxyaldehyde.

EXAMPLE 28

3,7-dimethyl-9-(2,4,5-trimethyl-3-thienyl)-2,4,6,8-nonatetraenoic acid ethyl ester 1.7 G. of 8-diethoxy-phosphono-3,7-dimethyl-octa-2,4,6-trienoic acid ethyl ester are introduced in 8.0 ml. of tetrahydrofuran. The solution is cooled to 0° C. after addition of 0.27 g. of sodium hydride (50–60%), then stirred 30 minutes at 0° C. and thereafter a solution of 1.0 of 2,4,5-trimethyl-3-thiophenecarboxaldehyde in 5 ml. of tetrahydrofuran is added dropwise during 15 minutes. The reaction mixture is stirred 7 hours at room temperature, then poured into ice and after addition of 2 N hydrochloric acid, extracted with diethyl ether. The ether extract is washed neutral with water, dried over sodium sulfate and evaporated under reduced pressure. The remaining 3,7-dimethyl-9-(2,4,5-trimethyl-3-thienyl)-2,4,6,8-nonatetraenoic acid ethyl ester is recrystallized from hexane, m.p. 88–89° C. Instead of sodium hydride (0.27 g.), employed above, an alkali metal alcoholate can also be used as condensation agent, e.g., sodium ethylate (0.125 g. of sodium in 5 ml. ethanol).

EXAMPLE 29

3,7-dimethyl-9-(2,4,5-trimethyl-3-thienyl)-2,4,6,8-nonatetraenoic acid ethyl ester 1.9 G. of 2,4,5-trimethyl-3-thiophenecarboxaldehyde and 6.75 g. of (7-ethoxycarbonyl-2,6-dimethyl-2,4,6-heptatrienyl)triphenyl phosphonium bromide are dissolved in 50 ml. of dry dimethylformamide. The solution is treated at 10° C. dropwise with a solution of 0.29 g. of sodium in 8 ml. of ethanol. The mixture is subsequently stirred for 4 hours at room temperature, then introduced into 100 ml. of methanol/water 60:40 parts by volume and thoroughly extracted with hexane. The hexane extract is washed with methanol/water (60:40 parts by volume, then with water, dried over sodium sulfate and evaporated. There is obtained 3,7-dimethyl-9-(2,4,5-trimethyl-3-thienyl)-2,4,6,8-nonatetraenoic acid ethyl ester, which melts after recrystallization from hexane at 88°–89° C.

EXAMPLE 30

8-hydroxy-3,7-dimethyl-octa-2,4,6-trien-1-oic acid ethyl ester

36 G. of 7-formyl-3-methyl-octa-2,4,6-trien-1-oic acid ethyl ester are dissolved in 600 ml. of absolute ethanol. The solution is treated portionwise with 1.8 g. of sodium borohydride. The mixture is stirred for 2 hours at 10° C. then poured onto ice water and 3 N aqueous hydrochloric acid and extracted with ether. The ether extract is washed successively with water, a saturated aqueous sodium bicarbonate solution and once more with water, dried over sodium sulfate and evaporated. There is obtained 8-hydroxy-3,7-dimethyl-octa-2,4,6-trien-1-oic acid ethyl ester.

EXAMPLE 31

8-bromo-3,7-dimethyl-octa-2,4,6-trien-1-oic acid ethyl ester 36.5 G. of 8-hydroxy-3,7-dimethyl-octa-2,4,6-trien-1-oic acid ethyl ester are dissolved in 380 ml. of ether. The solution is cooled to 0° C., and after the addition of 3 drops of pyridine treated dropwise with 28.6 g. of phosphorous tribromide in 120 ml. of hexane. The mixture is stirred for 20 minutes at 0° C., then poured onto ice water and extracted with ether. The ether extract is washed successively with water, a saturated aqueous sodium bicarbonate solution and again with water, dried over sodium sulfate and evaporated. There is obtained 8-bromo-3,7-dimethyl-octa-2,4,6-trien-1-oic acid ethyl ester.

EXAMPLE 32

1-ethoxycarbonyl-2,6-dimethyl-hepta-1,3,5-trien-7-triphenylphosphonium bromide 43.7 G. of 8-bromo-3,7-dimethyl-octa-2,4,6-trien-1-oic acid ethyl ester are dissolved in 500 ml. of benzene and treated with 42.0 g. of triphenylphosphine. The mixture is stirred for 12 hours at room temperature, then cooled at 0° C. The precipitated 1-ethoxycarbonyl-2,6-dimethyl-hepta-1,3,5-trien-7-triphenylphosphonium bromide melts at 193°–194° C.

EXAMPLE 33

2,4-dimethyl-5-chloro-thiphene 2.5 G. of 2,4-dimethyl-thiophene are dissolved in 45 ml. of methylene dichloride and 3.3 g. of sulfuryl chloride are dropped in. The mixture is kept at room temperature for 0.5 hour and then refluxed for 2 hours. The reaction mixture is poured into water, extracted with hexane, washed with saturated sodium chloride solution, dried over sodium sulfate, filtered and evaporated. Distillation gave 2,4-dimethyl-5-chloro-thiophene, b.p. 73–75° C./18 mm.

EXAMPLE 34

2,4-dimethyl-3-chloromethyl-5-chloro-thiophene 3.04 G. of 2,4-dimethyl-5-chloro-thiophene are dissolved in 60 ml. of acetic acid and 2.1 g. of formalin and 32 ml. of concentrated hydrochloric acid are added. The mixture is stirred at room temperature for 2 hours, then poured into ice water and extracted with hexane. The organic solution is washed with 5% sodium bicarbonate solution, dried, filtered and evaporated to yield 2,4-dimethyl-3-chloromethyl-5-chloro-thiophene.

EXAMPLE 35

(2,4-dimethyl-5-chloro-3-thenyl)triphenyl phosphonium chloride (2,4-dimethyl-5-chloro-3-thenyl)triphenyl phosphonium chloride can be prepared in a manner analogous to that described in Example 13 by reaction of 2,4-dimethyl-3-chloromethyl-5-chloro-thiophene with triphenyl phosphine, m.p. 246°–251° C.

EXAMPLE 36

All trans-3,7-dimethyl-9-(2,4-dimethyl-5-chloro-3-thienyl)-2,4,6,8-nonatetraenoic acid ethyl ester By the procedure of Example 14 (2,4-dimethyl-5-chloro-3-thenyl)triphenyl phosphonium chloride is condensed with 7-formyl-3-methyl-octa-2,4,6-trienoic acid ethyl ester to form all trans-3,7-dimethyl-9-(2,4-dimethyl-5-chloro-3-thienyl)-2,4,6,8-nonatetraenoic acid ethyl ester, which is recrystallized from hexane. m.p. 109°–110° C.

EXAMPLE 37

Ethyl-3,7-dimethyl-9-(2,5-dichloro-3-thienyl)-nona-2,4,6,8-tetraenoate

To a cold (−10° C.) suspension of 1.02 g. (2 mmoles) of crude (2,5-dichloro-3-thenyl)-triphenyl phosphonium bromide in 20 ml. of dry ether, 0.82 ml. (2 mmoles) of a 2.45 M solution of n-butyl lithium in hexane was added slowly via a syringe. After the addition was complete, the mixture was allowed to stir at −10° C. for 10 minutes. Then a solution of 416 mg. (2 mmoles) of ethyl 3,7-dimethyl-7-formyl-2,4,6-octatrienoate was added at 0°–2° C. The mixture was allowed to warm up to room temperature for 1½ hours and poured into 25 ml. of sodium chloride solution. Some brown solid was filtered off and the organic layer of the filtrate was separated and washed with two 50 ml. portions of sodium chloride solution, and dried over sodium sulfate. Evaporation of the solvent gave a yellow solid which was extracted with several 25 ml. of hexane. The hexane extracts were combined and concentrated to yield a yellow solid which was purified by chromatography on 45 g. of silica gel packed in hexane containing 2% ether. Elution with this solvent mixture gave ethyl 3,7-dimethyl-9-(2,5-dichloro-3-thienyl)-nona-2,4,6,8-tetraenoate.

EXAMPLE 38

(2,5-dichloro-3-thenyl)triphenyl phosphonium bromide 2,5-Dichloro-3-bromomethyl thiophene (22 g., 90 mmoles) was mixed with 26 g. (99 mmoles) of triphenyl phosphine and 150 ml. of benzene. The mixture was heated to the reflux for 2½ hours, cooled and filtered to give (2,5-dichloro-3-thenyl)triphenyl phosphonium bromide, m.p. 208°–215° C.

EXAMPLE 39

Wet Granulation Formulation—250 mg. tablets

|  | Per Tablet |
|---|---|
| all trans-N-ethyl-3,7-dimethyl-9-(2,4,5-trimethyl-3-thienyl)-2,4,6,8-nonatetraenamide - 2% excess | 255 mg. |
| Modified Starch | 25 mg. |
| Pregelatinized starch | 25 mg. |
| Microcrystalline cellulose | 35 mg. |
| Lactose anhydrous | 30 mg. |
| Magnesium stearate | 3 mg. |
| Talc | 7 mg. |
| Total Weight | 380 mg. |

Procedure:

1. Mix all ingredients, except items No. 6 and 7, in a suitable mixer. Mill and mix.
2. Granulate with water to a uniform wet consistency. Mill and spread it on trays.
3. Dry overnight in a suitable dryer.
4. Mill and prepare a premix with magnesium stearate and talc. Mix for 5 minutes.
5. Compress on a suitable press.

EXAMPLE 40

Direct Compression Formulation—25 mg. tablets

|  | Per Tablet |
|---|---|
| all trans-N-ethyl-3,7-dimethyl-9-(2,4,5-trimethyl-3-thienyl)-2,4,6,8-nonatetraenamide - 2% excess | 25.5 mg. |
| Lactose anhydrous | 172.5 mg. |
| Microcrystalline cellulose (pH 101) | 25 mg. |
| Starch | 25 mg. |
| Magnesium stearate | 2 mg. |
| Total Weight | 250 mg. |

Procedure:

1. Mix all ingredients, except item No. 5, in a suitable mixer.
2. Make a premix with magnesium stearate and add to the mix in Step 1. Mix for 5 minutes.
3. Compress on a suitable press.

EXAMPLE 41

Direct Compression Formulation—25 mg. tablets

|  | Per Tablet |
|---|---|
| all trans-3,7-dimethyl-9-(2,4,5-trimethyl-3-thienyl)-2,4,6,8-nonatetraenoic acid ethyl ester - 2% excess | 25.5 mg. |
| Lactose anhydrous | 172.5 mg. |
| Microcrystalline cellulose (pH 101) | 25 mg. |
| Starch | 25 mg. |
| Magnesium stearate | 2 mg. |
| Total Weight | 250 mg. |

Procedure:

1. Mix all ingredients, except item No. 5, in a suitable mixer.
2. Make a premix with magnesium stearate and add to the mix in Step 1. Mix for 5 minutes.
3. Compress on a suitable press.

EXAMPLE 42

Wet Granulation Formulations—250 mg. tablets

|  | Per Tablet |
|---|---|
| all trans-3,7-dimethyl-9-(2,4,5-trimethyl-3-thienyl)-2,4,6,8-nonatetraenoic acid ethyl ester - 2% excess | 255 mg. |
| Modified Starch | 25 mg. |
| Pregelatinized starch | 25 mg. |
| Microcrystalline cellulose | 35 mg. |
| Lactose anhydrous | 30 mg. |
| Magnesium stearate | 3 mg. |
| Talc | 7 mg. |
| Total Weight | 380 mg. |

Procedure:

1. Mix all ingredients, except items No. 6 and 7, in a suitable mixer. Mill and mix.
2. Granulate with water to a uniform wet consistency. Mill and spread it on trays.
3. Dry overnight in a suitable dryer.
4. Mill and prepare a premix with magnesium stearate and talc. Mix for 5 minutes.
5. Compress on a suitable press.

EXAMPLE 43

3-chloromethyl-2,5-dimethylthiophene 36.4 G., 0.325 mol. of 2,5-dimethylthiophene, 24.7 g. (0.307 mol) of freshly distilled chloromethyl methyl ether (b.p. 58°–60° C.) and 87.0 g. of glacial acetic acid were combined in a glass pressure bomb and stirred at room temperature for 5 hours. After 0.5 to 1 hr. an exothermic reaction took place. The reaction mixture was cooled externally in an ice bath so that the reaction temperature did not exceed 35° C. The color of the mixture changed from green to blue. The resulting solution was poured into ice water, stirred for ten minutes and extracted four times with benzene. The combined benzene extracts were washed twice with saturated sodium chloride solution, dried and evaporated. The resulting liquid was quickly distilled and the material which boiled at 90°–125° C./18 mm. was collected. A second distillation yielded the pure product, b.p. 109°–115° C./18 mm.

EXAMPLE 44

2,3,5-trimethylthiophene

9 G. of Pd-C (5%) were added to a solution of 44.0 g. (0.274 mol) of 2,5-dimethyl-3-chloromethyl-thiophene in 500 ml. of ether and 41.5 g. (0.41 mol) of triethylamine (57 ml.). The resulting reaction mixture was hydrogenated under low pressure (200 psi) at room temperature. Additional catalyst is added until no more hydrogen was taken up. The reaction took approximately 6 hrs. and about 6.1 l. of hydrogen was taken up. The catalyst was filtered off and the solvent was evaporated at normal pressure on a small Vigreux column. Distillation of the resulting liquid gave the final product, 2,3,5-trimethylthiophene, b.p. 85°–89° C./61 mm.

EXAMPLE 45

3-ethoxycarbonyl-4-methyl-hexane-2,5-dione 7.3 G., 0.317 mol of sodium was dissolved in 125 ml. of absolute ethanol 87.0 G. (0.669 mol) of ethyl acetoacetate were added to the resulting solution of sodium ethoxide in the cold. The reaction mixture was heated to reflux and 48.6 g. (0.322 mol) of freshly distilled 3-bromo-2-butanone were added dropwise with stirring over a period of 30 min. Refluxing was continued until the mixture tested neutral to pH paper (~1.5 hrs.). The precipitated sodium bromide was filtered off the cold solution and most of the ethanol was removed on an evaporator. The mixture was filtered again and distilled. The 3-ethoxycarbonyl-4-methyl-hexane-2,4-dione fraction which boiled at 131°–137° C./18 mm. was collected.

EXAMPLE 46

3-methyl-hexane-2,5-dione

A mixture of 3.0 g. (0.15 mol) of 3-ethoxycarbonyl-4-methyl-hexane-2,4-dione, 30.0 g. (0.217 mol) of potassium carbonate and 120 ml. of water was refluxed for 4 hrs. under vigorous stirring (oil-bath temperature 120° C.). The reaction mixture which was cold was then diluted with ether, the ether layer separated and the aqueous phase was extracted again with ether. The combined organic phases were washed with sodium chloride solution, dried and evaporated. The residue was distilled under reduced pressure to yield 3-methyl-hexane-2,5-dione, b.p. 79°–84° C./18 mm.

EXAMPLE 47

2,3,5-trimethylthiophene 10.6 G. (0.083 mol) of 3-methyl-hexane-2,5-dione was added slowly to 7.4 g. (0.033 mol) of phosphorus pentasulfide under stirring and cooling with an ice bath. The resulting reaction mixture was allowed to warm to room temperature and then heated slowly under vigorous stirring to 65°–70° C. At this temperature, a vigorous reaction took place (hydrogen sulfide development). Heating was discontinued. After 10 min. the reaction had subsided and the mixture was heated slowly to 160° C. and kept at this temperature for 3 hrs. with the addition of 1.0 g. of phosphorus pentasulfide after the first half hour. The liquid was distilled away from the tarry residue between 157°–165° C. The crude product was refluxed for 15 min. over about 0.5 g. of sodium and then distilled to yield 2,3,5-trimethylthiophene, b.p. 85°–89° C./61 mm.

EXAMPLE 48

2,3,4-trimethylthiophene 12.3 G. (0.0385 mol) of 2,3,4-tribromothiophene was dissolved in 1 l. of dry ether. The resulting solution was cooled to −78° C. and a precooled solution of 1.0 mol. of n-butyl lithium (2.4 molar) in hexane was added dropwise. The reaction mixture was stirred for 3 hrs. at −78° C. After the dropwise addition of a precooled solution of 126 g. (1.0 mol. 94.7 ml.) of dimethyl sulfate in 300 ml. of ether, stirring was continued at −78° C. for one hour. The reaction mixture then was allowed to warm up to room temperature and a solution of 48 g. (1.2 mol) of sodium hydroxide in 600 ml. of water was added slowly. After 2 hrs., the resulting layers were separated. The organic phase was washed three times with water, dried and evaporated. Distillation of the residue gave trimethylthiophene, b.p. 67°–69° C./18 mm.

EXAMPLE 49

3,4,5-trimethylthiophene-2-carboxaldehyde

A mixture of 4.32 g. (0.032 mol) of N-methyl-formanilide, 4.90 g. (0.032 mol) of phosphorus oxychloride and 4.04 g. (0.032 mol) of 2,3,4-trimethylthiophene was warmed briefly on a steam bath until evolution of hydrogen chloride began. The heat was removed and, if necessary, the reaction was moderated by cooling. After stirring at room temperature overnight, ice and ether were added and the mixture was stirred for one hour. The phases were separated and the aqueous layer was extracted three times with ether. The combined organic phases were washed twice with 6 N hydrochloric acid, water, sodium bicarbonate and water, dried and evaporated. The residue was recrystallized from 75% ethanol/water to yield 3,4,5-trimethylthiophene-2-carboxaldehyde, m.p. 45°–46° C.

EXAMPLE 50

2-hydroxymethyl-3-methylthiophene 0.95 G. (0.025 mol) of sodium borohydride were added in portions to a solution of 12.6 g. (0.1 mol) of 3-methylthiophene-2-carboxaldehyde in 150 ml. of ethanol. The resulting reaction mixture was stirred at room temperature for 0.5 hr., poured into ice water and extracted with ether. The organic phase was washed with saturated sodium chloride solution, dried and evaporated. The residue was distilled to yield 2-hydroxymethyl-3-methylthiophene, b.p. 46° C./0.3 mm.

EXAMPLE 51

All trans-3,7-dimethyl-9-(3-methyl-2-thienyl)-2,4,6,8-nonatetraenoic acid ethyl ester 1.16 G. of a 50% suspension in mineral oil, (23 mmol) of sodium hydride was washed with pentane, dried and suspended in 50 ml. of dry dimethylformamide. A suspension of 7.5 g. (16.4 mmol) of (3-methyl-2-thenyl)-triphenylphosphonium bromide in 25 ml. of dimethylformamide was added dropwise. The resulting reaction mixture was stirred for 15 minutes. A solution of 3.74 g. (18 mmol) of ethyl 7-formyl-3-methyl-2,4,6-octatrienoate in 20 ml. of DMF was added slowly. After stirring for 2.5 hours at room temperature, the reaction mixture was poured into a methanol/water mixture (ratio 6:4) and extracted several times with hexane. The combined organic phases were washed once with methanol/water (6:4); dried and evaporated. The crude product was recrystallized from hexane to yield all trans-3,7-dimethyl-9-(3-methyl-2-thienyl)-2,4,6,8-nonatetraenoic acid ethyl ester.

EXAMPLE 52

2-hydroxymethyl-5-methylthiophene 0.55 G. (15 mmol) of sodium borohydride were added in portions to a solution of 7.0 g. (56.0 mmol) of 5-methylthiophene-2-carboxaldehyde in 100 ml. of ethanol. The resulting reaction mixture was stirred at room temperature for 0.5 hr., poured into ice water and extracted with ether. The organic phase was washed with saturated sodium chloride solution, dried and evaporated. The residue was distilled to yield 2-hydroxymethyl-3-methylthiophene.

EXAMPLE 53

2-chloromethyl-3,4-tribromothiophene 4.07 G. (50 mmol) of formalin (37%) and 40 ml. of concentrated hydrochloric acid were added to a solution of 10.2 g. (33.3 mmol) of 3,4,5-tribromothiophene in 20 ml. of acetic acid. The resulting mixture was warmed to 70° C. After 6 hrs., 4.07 g. of formalin were added and heating was continued overnight. The resulting mixture was cooled, poured on ice water and extracted with ether. The organic phase was washed twice with water, sodium bicarbonate and water, dried and evaporated to give crude 2-chloromethyl-3,4,5-tribromothiophene.

EXAMPLE 54

2,4,6-trans-8-cis-3,7-dimethyl-9-(3,4,5-tribromo-2-thienyl)-2,4,6,8-nonatetraenoic acid ethyl ester and all trans-3,7-dimethyl-9-(3,4-dibromo-2-thienyl)-2,4,6,8-nonatetraenoic acid ethyl ester Sodium hydride (1.04 g. of a 50% suspension in mineral oil, 21.6 mmol) was washed with pentane, dried and suspended in 100 ml. of dry dimethylformamide. At 0° C., 13.0 g. (20.6 mmol) of (3,4,5-tribromo-2-thienyl)-triphenyl phosphonium chloride were added in small portions to the suspension. After stirring for 20 min., a solution of 4.70 g. (22.6 mmol) of ethyl-7-formyl-3-methyl-2,4,6-octatrienoate in 30 ml. of dimethylformamide was added slowly. The resulting reaction mixture was stirred at 0°-5° C. for one hour, poured into a methanol/water mixture (ratio 6:4) and extracted several times with hexane. The combined organic phases were washed once with methanol/water (6:4), dried and evaporated. The crystalline crude material which resulted was filtered through a short column (silica gel, hexane/ethyl acetate 4:1). The filtrate was evaporated and separated by preparative high pressure liquid chromatography. The two main fractions of the LC-separation were recrystallized from hexane to yield pure 2,4,6-trans-8-cis-3,7-dimethyl-9-(3,4,5-tribromo-2-thienyl)-2,4,6,8-nonatetraenoic acid ethyl ester, m.p. 84°-86° C., and pure all trans-3,7-dimethyl-9-(3,4-dibromo-2-thienyl)-2,4,6,8-nonatetraenoic acid ethyl ester, m.p. 106°-110° C.

EXAMPLE 55

All trans-3,7-dimethyl-9-(3,4,5-tribromo-2-thienyl)-2,4,6,8-nonatetraenoic acid ethyl ester Three crystals of iodine were added to a solution of 2.3 g. (4.38 mmol) of 2,4,6-trans-8-cis-3,7-dimethyl-9-(3,4,5-tribromo-2-thienyl)-2,4,6,8-nonatetraenoic acid ethyl ester in 100 ml. of benzene and then stirred at room temperature overnight. The resulting solution was washed once with 1 N sodium thiosulfate and water, dried and evaporated. The crude product was purified by chromatography (silica gel, methylene chloride) to yield after recrystallization from 50% hexane/ethyl acetate pure all trans-3,7-dimethyl-9-(3,4,5-tribromo-2-thienyl)-2,4,6,8-nonatetraenoic acid ethyl ester, m.p. 158°-159° C.

EXAMPLE 56

2-methyl-3,4-dibromothiophene 37.6 Ml. (90.2 mmol) of a solution of n-butyl lithium in hexane (22%, 2.4 ml.) were slowly added at −78° C. to a solution of 29.0 g. (90.2 mmol) of tribromothiophene in 600 ml. of dry ether. The resulting reaction mixture was stirred at −78° C. for 1.5 hrs. 9.0 ml. (95 mmol) of dimethylsulfate were slowly added. After stirring at −78° C. for another hour, the reaction mixture was allowed to warm up to room temperature and was stirred for one hour. A solution of 4.8 g. (0.12 mol) of sodium hydroxide in 150 ml. of water was added and the resulting mixture was stirred for two hours at room temperature. The phases were separated, the ether layer washed with water, dried and evaporated. The remaining liquid was quickly distilled and the fraction which boiled at 54°-60° C./0.5 mm. was again distilled using a Vigreux-column to yield 2-methyl-3,4-dibromothiophene, b.p. 38°-42° C./0.25 mm.

EXAMPLE 57

All trans and 2,4,6-trans-8-cis-3,7-dimethyl-9-(3,4-dibromo-5-methyl-2-thienyl)-2,4,6,8-nonatetraenoic acid ethyl ester A suspension of 16.64 g. (29.4 mmol) of phosphonium chloride and 6.72 g. (32.3 mmol) of ethyl-7-formyl-3-methyl-2,4,6-octatrienoate in 300 ml. of butylene oxide were heated to 70° C. for 15 hrs. The resulting clear solution was cooled and the solvent evaporated. The residue was dissolved in hexane/ethyl acetate (ratio 1:1) and filtered through a short column (silica gel). The resulting filtrate was evaporated to a volume of about 100ml. The crystals which precipitated were filtered and recrystallized from hexane/ethyl acetate (1:1) to yield all trans-2,4,6,8-3,7-dimethyl-9-(3,4-dibromo-5- methyl-2-thienyl)-2,4,6,8-nonatetraenoic acid ethyl ester, m.p. 150°–153° C.

Preparative LC of the filtrate yielded after recrystallization from hexane a mixture of 80% 2,4,6-trans-8-cis-3,7-dimethyl-9-(3,4-dibromo-5-methyl-2-thienyl)-2,4,6,8-nonatetraenoic acid ethyl ester and 20% of the all-trans isomer m.p. 73°–76° C.

EXAMPLE 58

Alpha-mercapto-acetone

A solution of 48 g. (1.2 mol) of sodium hydroxide in 300 ml. of water was cooled to 0° C. and saturated with hydrogen sulfide. Freshly distilled chloroacetone (105 g., 1.1 mol, b.p. 108°–110° C.) was slowly added. During the addition the reaction temperature should not be higher than 0° C. (acetone/dry ice bath). The reaction mixture was stirred at 0° C. for thirty minutes. The resulting white precipitate was filtered, washed well with cold water, alcohol and ether and dried at room temperature under high vacuum to yield the dimer of alpha-mercapto-acetone. m.p. 108°–111° C.

EXAMPLE 59

2,4-dimethyl-2,5-dihydrothiophene

Two ml. of dry triethylamine were added to a suspension of 170 g. (0.44 mol) of (allyl)-triphenyl phosphonium bromide in one liter of dry pyridine. After one hour of stirring at room temperature, 70 g. (0.68 mol) of dry triethylamine were added. Stirring was continued for an additional thirty minutes. After adding 40 g. (0.44 mol) of alpha-mercapto-acetone dimer to the resulting yellow clear solution, the reaction mixture was refluxed for 20 hrs. (oil bath 120° C.) under argon. The mixture was cooled, poured into ice water, neutralized with 12 N hydrochloric acid and extracted four times with a mixture of pentane/ether (ratio 1:1). The combined organic phases were washed with 3 N hydrochloric acid and sodium chloride solution. The dried solvent was evaporated at normal pressure using a Vigreux-column. The resulting precipitated triphenylphosphine oxide was filtered, was well with cold pentane and the filtrate distilled again to yield 2,4-dimethyl-2,5-dihydrothiophene as a colorless liquid, b.p. 101°–103° C./150 mm.

EXAMPLE 60

2,4-dimethylthiophene

A solution of 22.4 g. (0.124 mol) of 2,4-dimethyl-2,5-dihydrothiophene in 100 ml. of dry benzene was heated to reflux and a solution of 51.0 g. (0.225 mol) of DDQ in 1400 ml. of dry benzene was added through a dropping funnel. The resulting reaction mixture was heated for another hour, then cooled and filtered. The precipitate was washed well with ether. The filtrate was washed several times with 5% sodium bicarbonate solution and dried with sodium sulfate. The solvent was evaporated at normal pressure using a Vigreux-column. Distillation of the residue yielded 2,4-dimethylthiophene as a colorless liquid, b.p. 98°–101° C./180 mm.

EXAMPLE 61

All trans-3,7-dimethyl-9-(2,4-dimethyl-5-chloro-3-thienyl-2,4,6,8-nonatetraneoic acid ethyl ester A mixture of 6.74 g. (14.7 mmol) of (5-chloro-2,4-dimethyl-3-thenyl)triphenyl phosphonium chloride, 3.15 g. (15.1 mmol) of ethyl 7-formyl-3-methyl-2,4,6-octatrienoate and 300 ml. of butylene oxide was refluxed until the solution became clear (about 22 hrs.). The clear solution was cooled, poured into 500 ml. of a methanol/water mixture (ratio 6:4) and extracted with hexane. The combined hexane extracts were washed with methanol/water (6:4), dried and evaporated. The resulting crude material was purified by chromatography (silica gel, hexane/ether=4:1) to yield after recrystallization from hexane, all trans-3,7-dimethyl-9-(2,4-dimethyl-5-chloro-3-thienyl)-2,4,6,8-nonatetraenoic acid ethyl ester, m.p. 109°–110° C.

EXAMPLE 62

2-methyl-3,5-dichlorothiophene 78.2 G. (0.58 mol) of sulfuryl chloride were slowly added to a solution of 29.4 g. (0.3 mol) of 2-methylthiophene in 300 ml. of methylene chloride. The resulting reaction mixture was stirred overnight at room temperature, poured into ice water and extracted with hexane. The hexane solution was washed with water, 1 N sodium bicarbonate and water, dried and evaporated. The resulting liquid residue was distilled, b.p. 30°–60° C./0.15 mm. (28.5 g.).

According to GC this material contained 68% of 2-methyl-3,5-dichlorothiophene. The main side product was 2-chloro-5-methylthiophene. A second distillation using a Vigruex column yielded almost pure 2-methyl-3,5-dichlorothiophene, b.p. 62°–65° C./10 mm.

EXAMPLE 63

3-chloromethyl-2,4-dichloro-5-methylthiophene 8.6 G. (0.107 mol) of formalin and 90 ml. concentrated hydrochloric acid were added to a solution of 10.87 g. (0.065 mol) of 2-methyl-3,5-dichlorothiophene in 45 ml. of acetic acid. The resulting mixture was heated to 70° C. for 18 hrs., cooled, poured into ice water and extracted with ether. The organic solution was washed with water, sodium bicarbonate and water, dried and evaporated to yield 3-chloromethyl-2,4-dichloro-5-methylthiophene as a crude oil.

EXAMPLE 64

(2,4-dichloro-5-methyl-3-thenyl)triphenyl phosphonium chloride

A mixture of 13.1 g. (~0.061 mol) of crude 3-chloromethyl-2,4-dichloro-5-methylethiophene, 26.2 g. (0.10 mol) of triphenylphosphin and 200 ml. of toluene was warmed to 100° C. for 20 hrs., then cooled to room temperature. The resulting precipitate was collected by filtration, washed with cold benzene and dried at 80° C. under high vacuum to yield (2,4-dichloro-5-methyl-5-thenyl)triphenyl phosphonium, m.p. 211°214° C.

EXAMPLE 65

All trans-3,7-dimethyl-9-(2,4-dichloro-5-methyl-3-thienyl)-2,4,6,8-nonatetraenoic acid ethyl ester A suspension of 10.83 g. (22.6 mmol) of (2,4-dichloro-5-methyl-3-thenyl)triphenyl phosphonium chloride and 5.15 g. (24.8 mmol) of ethyl 7-formyl-3-methyl-2,4,6-octatrienoate in 350 ml. of butylene oxide was heated to 70° C. for 4.5 hrs. The resulting clear solution was cooled, poured into 500 ml. of a methanol/water mixture (6:4) and extracted with hexane. The combined hexane extracts were washed with methanol/water (6:4), dried and evaporated. The resulting crude material was purified by chromatography (silica gel, hexane/ethyl acetate=4:1) to yield after recrystallization from hexane, all trans-3,7-dimethyl-9-(2,4-dichloro-5-methyl-3-thienyl)-2,4,6,8-nonatetraenoic acid ethyl ester, m.p. 99°-100° C.

EXAMPLE 66

2,4-diethoxycarbonyl-3-methyl-5-acetylamino-thiophene

A solution of 23.0 g. (0.09 mol) of 2,4-diethoxycarbonyl-3-methyl-5-aminothiophene in 250 ml. of acetic anhydride was heated to 100° C. for 1.5 hrs. The resulting mixture was cooled in an ice bath and the precipitated crystals were filtered to yield 2,4-diethoxycarbonyl-3-methyl-5-acetylamino-thiophene, m.p. 130°-131° C.

EXAMPLE 67

2,4-diethoxycarbonyl-3-bromomethyl-5-acetylamino-thiophene 10.5 G. (59 mmol) of N-bromo-succinimide and 20 mg. of benzoylperoxide were added to a solution of 17.5 g. (59 mmol) of 2,4-dethoxycarbonyl-3-methyl-5-acetylamino-thiophene in 250 ml. of carbontetrachloride. The resulting mixture was refluxed for 24 hrs., until all solid material was floating on the surface. After one and seven hours respectively were added 20 mg. of benzoylperoxide. Because a separation of the product 2,4-diethoxycarbonyl-3-bromomethyl-5-acetylamino-thiophene and succinimide proved to be very difficult, the crude product, an intermediate was used without further purification.

EXAMPLE 68

(2,4-diethoxycarbonyl-5-acetylamino-3-thenyl)-triphenyl phosphonium bromide 22.2 G of crude 2,4-diethoxycarbonyl-3-bromomethyl-5-acetylaminothiophene, 19.7 g. (75 mmol) of triphenylphosphine and 700 ml. of toluene were refluxed for 3 hrs. The resulting precipitate was filtered from the hot solution and washed well with toluene to yield (2,4-diethoxycarbonyl-5-acetylamino-3-thenyl)triphenyl phosphonium bromide, m.p. 186°-195° C. The NMR-spectrum showed that the material contained 11% of succinimide.

EXAMPLE 69

All trans-3,7-dimethyl-9-(2,4-diethoxycarbonyl-5-acetylamino-3-thienyl)-2,4,6,8-nonatetraenoic acid ethyl ester A suspension of 30.0 g. (~47 mmol, containing 11% of succinimide) of (2,4-diethoxycarbonyl-5-acetylamino-3-thenyl)triphenyl phosphonium bromide and 9.75 g. (47 mmol) of ethyl-7-formyl-3-methyl-2,4,6-octatrienoate in a mixture of 500 ml. of toluene and 100 ml. of butylene oxide was refluxed until the solution was clear (for three hours). The resulting solution was cooled and the solvent evaporated. The residue which resulted was suspended in 600 ml. of a methanol/water (ratio 6:4) mixture and one liter of hexane and stirred for 0.5 hr. The insoluble material was filtered and boiled with 3 l. of hexane. The insoluble material was filtered from the cold solution, washed with hexane and purified by chromatography (silica gel), ethyl acetate). Recrystallization of the purer fractions from hexane/40% ethyl acetate yielded all trans-3,7-dimethyl-9-(2,4-diethoxy-carbonyl-5-acetylamino-3-thienyl)-2,4,6,8-nonatetraenoic acid ethyl ester, m.p. 159°-161° C.

EXAMPLE 70

2-hydroxymethyl-3-methyl-5-iodothiophene 6.58 G. (33 mmol) of mercuric oxide and 7.62 g. (30 mmol) of iodine were added alternately in small amounts to a vigorously stirred solution of 3.84 g. (30 mmol) of 2-hydroxymethyl-3-methylthiophene in 30 ml. of benzene. The reaction was kept at room temperature by cooling with an ice bath. The orange mercuric iodide which precipitated was filtered and washed well with benzene. The combined organic solutions were washed with sodium thiosulfate and saturated sodium chloride solution, dried and evaporated to yield crude 2-hydroxymethyl-3-methyl-5-iodothiophene as a colorless oil.

EXAMPLE 71

2-hydroxymethyl-3-methyl-5-methoxythiophene 10.0 G. (0.125 mol) of cupric oxide and 11.0 g. (0.0433 mol) of 2-hydroxymethyl-3-methyl-5-iodothiophene was added to a solution of 10.0 g. (0.435 mol) of sodium in 90 ml. of methanol. The resulting reaction mixture was heated to 80° C. for 18 hrs. with vigorous stirring. The cold solution was filtered, the filtrate poured into ice water and extracted with ether/hexane (ratio 4:1). The organic extracts were washed with 10% sodium thiosulfate solution and saturated sodium chloride solution, dried and evaporated to yield 2-hydroxymethyl-3-methyl-5-methoxythiophene as a colorless oil.

EXAMPLE 72

(3-methyl-5-methoxy-2-thenyl)triphenylhosphonium chloride 21.0 G. (80.2 mmol) of triphenylphosphine were added to a solution of 5.8 g. (36.7 mmol) of 2-hydroxymethyl-3-methyl-5-methoxythiophene in 60 ml. of dry carbon tetrachloride and 80 ml. of toluene. The temperature of the reaction mixture was slowly raised to 80° C. and heating was continued overnight. The resulting precipitate was filtered from the cold solution, washed well with cold benzene and dried in high vacuum to yield (3-methyl-5-methoxy-2-thenyl)triphenyl phosphonium chloride, m.p. 180°-185° C.

EXAMPLE 73

All trans-3,7-dimethyl-9-(3-methyl-5-methoxy-2-thienyl)-2,4,6,8-nonatetraenoic acid ethyl ester A suspension of 5.9 g. (13.5 mmol) of (3-methyl-5-methoxy-2-thenyl)triphenyl phosphonium chloride and 2.81 g. (13.5 mmol) of ethyl-7-formyl-3-mehtyl-2,4,6-octatrienoate in 70 ml. of butylene oxide and 200 ml. of toluene was heated to 100° C. for 14 hrs. The resulting clear solution was cooled, poured into 500 ml. of a methanol/water mixture (6:4) and extracted with hexane. The combined hexane extracts were washed with methanol/water (6:4), dried and evaporated. The resulting crude, oily material was purified by chromatography (silica gel, hexane/ether, ratio 7:3) to yield after recrystallization from hexane all trans-3,7-dimethyl-9-(3-methyl-5-methoxy-2-thienyl)-2,4,6,8-nonatetraenoic acid ethyl ester, m.p. 66°-72° C.

EXAMPLE 74

2,4-dimethyl-3,5-dibromothiophene

A solution of 47.36 g. (0.296 mol) of bromine in 500 ml. of dioxane was slowly added to a solution of 16.58 g. (0.148 mol) of 2,4-dimethylthiophene in 150 ml. of dioxane. The reaction mixture was kept at room temperature and stirring was continued for 18 hrs. The reaction mixture then was poured into ice water and extracted with ether. The combined organic layers were washed with 5% sodium carbonate and saturated sodium chloride solution, dried and evaporated using a Vigreux column. Distillation of the residue gave two fractions, b.p. 75°-79° C./0.3 mm. and b.p. 80°-81° C./0.2 mm. According to GC, fraction 1 was 89% pure, fraction 2 95% pure. The fractions were combined to yield 3,5-dibromo-2,4-dimethylthiophene.

EXAMPLE 75

2,4-dimethyl-3-bromothiophene

A solution of 36.0 g, (0.133 mol) of 2,4-dimethyl-3,5-dibromothiophene in 250 ml. of dry ether was cooled to −68° C. and 60 ml. of a hexane solution of n-butyl lithium (2.4 molar, 0.144 mol) was added dropwise. The reaction mixture was allowed to warm up to −32° C. for 15 min., cooled again to −70° C. and then quenched by adding 50 ml. of water. The resulting mixture was stirred for ten minutes, poured into ice water and extracted with ether/hexane (ratio 4:1). The combined organic layers were washed with 5% sodium carbonate and saturated sodium chloride solution, dried and evaporated using a Vigreux column. Distillation of the residue yielded 2,4-dimethyl-3-bromothiophene, b.p. 50°-51° C./10 mm.

EXAMPLE 76

2,4-dimethylthiophene-3-carboxaldehyde

A solution of 15 g. (79.0 mmol) of 2,4-dimethyl-3-bromothiophene in 120 ml. of dry ether was cooled to −70° C. and 36 ml. of a hexane solution of n-butyl lithium (2.4 molar, 86.4 mmol) were added dropwise. The reaction mixture was allowed to warm up to −20° C. for 10 min., cooled again to −70° C. and then quenched by adding dropwise 15 g. (0.205 mol) of dimethylformamide. The mixture was stirred at room temperature overnight, poured into ice water, stirred for 15 min. and extracted four times with ether. The ether phase was washed with saturated sodium chloride solution, dried and evaporated. The resulting oily residue was distilled to yield 2,4-dimethylthiophene-3-carboxaldehyde, b.p. 50°-55° C./0.1 mm.

EXAMPLE 77

2,4-dimethyl-3-hydroxymethylthiophene 0.68 G. (18 mmol) of sodium borohydride was added in three portions to a solution of 10.88 g. (72 mmol) of 2,4-dimethylthiophene-3-carboxaldehyde in 120 ml. of ethanol. After 15 min., the reaction mixture was poured into water, extracted with ether, dried and the solvent evaporated. The resulting residue was recrystallized from hexane to yield 2,4-dimethyl-3-hydroxymethylthiophene, m.p. 80° C.

EXAMPLE 78

2,4-dimethyl-3-hydroxymethyl-5-iodothiophene 10.0 G. (46 mmol) of mercuric oxide and 14.7 g. (58 mmol) of iodine were added alternately over a period of 1¼ hrs. to a vigorously stirred solution of 8.2 g. (57.7 mmol) of 2,4-dimethyl-3-hydroxymethylthiophene in 300 ml. of benzene. The reaction mixture was kept at room temperature by cooling with and ice bath and stirring was continued for an additional hour. The mercuric iodide which precipitated was filtered and washed well with warm ethyl ether. The combined organic solutions were washed with 10% sodium thiosulfate and saturated sodium chloride solution, dried and evaporated. The resulting residue was dissolved in a minimum amount of hot ether, an equal amount of hexane was added and the solution cooled to −50° C. The crystals which precipitated were filtered and washed with cold hexane to yield after drying 2,4-dimethyl-3-hydroxymethyl-5-iodothiophene, m.p. 118.5°-120.5° C.

EXAMPLE 79

2,4-dimethyl-3-hydroxymethyl-5-methoxythiophene 12.0 G. (0.151 mol) of cupric oxide and 12.5 g. (0.0466 mol) of 2,4-dimethyl-3-hydroxymethyl-5-iodothiophene were added to a solution of 12.5 g. (0.543 mol) of sodium in 100 ml. of dry methanol. The reaction mixture was heated to 80°-82° C. (internal temperature) for 20 hrs. with vigorous stirring, then cooled. The cold solution was diluted with 150 ml. of methanol, filtered, poured into ice water and extracted with ether/hexane (ratio 4:1). The organic layers were washed with 5% sodium carbonate solution, dried and evaporated. The residue which resulted was recrystallized from hexane to yield 2,4-dimethyl-3-hydroxymethyl-5-methoxythiophene, m.p. 55°-60° C. This product contained about 10% of 2,4-dimethyl-3-hydroxymethylthiophene which is formed in this reaction by reduction of the iodide. Fraction recrystallization of a sample from hexane yielded pure 2,4-dimethyl-3-hydroxymethyl-5-methylthiophene, m.p. 64°-65° C.

EXAMPLE 80

(2,4-dimethyl-5-methoxy-3-thenyl)-triphenylphosphonium bromide 6.1 G. (35.5 mmol) of 2,4-dimethyl-3-hydroxymethyl-5-methoxythiophene were added at 35° C. with vigorous stirring to a suspension of 13.4 g. (39.0 mmol) of triphenylphosphonium bromide in 250 ml. of acetonitrile. The deep purple color which was formed immediately, disappeared after some minutes. The reaction mixture was stirred for 3 hrs. The solvent was evaporated to a volume of about 25 ml. and an excess of cold ether was added. The solvent then was decanted from the resulting oily precipitate which was dissolved in warm acetone and again precipitated by adding cold ether. The solvent was decanted and the resulting oily residue was dried in high vacuum to yield (2,4-dimethyl-5-methoxy-3-thenyl)triphenylphosphonium bromide.

EXAMPLE 81

All trans-3,7-dimethyl-9-(2,4-dimethyl-5-methoxy-3-thienyl)-2,4,6,8-nonatetraenoic acid ethyl ester A suspension of 11.0 g. (22.1 mmol) of 2,4-dimethyl-5-methoxy-3-thenyl)triphenyl phosphonium bromide and 5.1 g. (24.5 mmol) of ethyl-7-formyl-3-methyl-2,4,6-octatrienoate in 450 ml. of butylene oxide was heated to 70° C. until a clear solution resulted (about 12 hours). The resulting clear solution was cooled, poured into 500 ml. of methanol/water (6:4) and extracted with hexane. The combined hexane extracts were washed with methanol/water (6:4) dried and evaporated. The resulting crude material was purified by column chromatography (silica gel, hexane/ether = 10:3) to yield after recrystallization from hexane, all trans-3,7-dimethyl-9-(2,4-dimethyl-5-methoxy-3-thienyl)-2,4,6,8-nonatetraenoic acid ethyl ester, m.p. 81°–82° C.

EXAMPLE 82

4-bromo-3,5-dimethylthiophene-2-carboxaldehyde 15.0 G. of 2,4-dibromo-3,5-dimethylthiophene was dissolved in 250 ml. of anhydrous ether and cooled to −70° C. with stirring under argon. 24 Ml. of a 2.4 M sodium of n-butyl lithium was slowly added to the solution and the mixture was warmed to −35° C. for 10 minutes, and then cooled again to −70° C. 7.3 G. of dimethylformamide was added slowly to the mixture and the reaction mixture was warmed to room temperature for 14 hours. The resulting solution was poured into ice water, stirred for 20 minutes and extracted with ethyl ether. The ether extracts were combined, washed with an aqueous solution of 5% sodium carbonate, saturated sodium chloride solution, dried with sodium sulfate, filtered and evaporated to yield 4-bromo-3,5-dimethylthiophene-2-carboxaldehyde, m.p. 44°–45° C.

EXAMPLE 83

4-bromo-3,5-dimethyl-2-hydroxymethylthiophene 11.8 G. of 4-bromo-3,5-dimethylthiophene-2-carboxaldehyde was dissolved in 250 ml. of dry ethanol and stirred at 20° C. 0.52 G. of sodium borohydride was added and the resulting solution was stirred for 30 minutes, then poured into ice water and extracted with ethyl ether. The combined ether extracts were washed with a solution of 5% sodium carbonate and a saturated sodium chloride solution, dried over sodium sulfate, filtered and evaporated. Crystallization from cold hexane yielded 4-bromo-3,5-dimethyl-2-hydroxymethylthiophene, m.p. 85°–90° C.

EXAMPLE 84

4-bromo-3,5-dimethyl-2-methoxymethylthiophene 2.9 G. of a 50% suspension of sodium hydride in mineral oil was washed once with pentane and suspended in 100 ml. of dimethylformamide at 5° C. 10.5 G. of a solution of 4-bromo-3,5-dimethyl-2-hydroxymethylthiophene in 40 ml. of dimethylformamide was added slowly to the suspension and stirred for 30 minutes. 10 G. of methyl iodide was added and the resulting mixture was stirred for 14 hours at 20° C. The reaction mixture was then poured into water and extracted with hexane. The hexane extracts were washed with a solution of 5% sodium carbonate, a saturated solution of sodium chloride, dried over sodium sulfate, filtered and evaporated to yield 4-bromo-3,5-dimethyl-2-methoxymethylthiophene.

EXAMPLE 85

2,4-dimethyl-5-methoxymethylthiophene-3-carboxaldehyde 15.5 G. of 4-bromo-3,5-dimethyl-2-methoxymethylthiophene was dissolved in 200 ml. of anhydrous ethyl ether under argon. The resulting solution was cooled to −70° C. and 22 ml. of a 2.4 M solution of n-butyl lithium was slowly added. The reaction mixture was warmed to −30° C. for 10 minutes and then cooled to −70° C. 7.3 G. of dimethylformamide was slowly added and reaction was warmed to room temperature for 14 hours. The resulting reaction mixture was poured into ice water, stirred for 15 minutes and extracted with ethyl ether. The combined ether extracts were washed with a solution of 5% sodium carbonate, a saturated solution of sodium chloride, drive over sodium sulfate, filtered and evaporated to yield 2,4-dimethyl-5-methoxymethylthiophene-3-carboxaldehyde.

EXAMPLE 86

Ethyl-3,7-dimethyl-9-(2,4-dimethyl-5-methoxymethyl-3-thienyl)-2,4,6,8-nonatetraenoate 3.6 G of a 50% suspension of sodium hydride in mineral oil was washed once with pentane, and suspended in 200 ml. of dimethylformamide at 5° C. 40.2 G. of a solution of triphenyl-(7-ethoxycarbonyl-2,6-dimethyl-2,4,6-heptatrienyl)phosphonium bromide in 75 ml. of dimethylformamide was added slowly and stirred for 30 minutes. 12.6 G. of a solution of 2,4-dimethyl-5-methoxymethylthiophene-3-carboxaldehyde in 50 ml. of dimethylformamide was then added slowly. The resulting reaction mixture was stirred at 5° C. for 10 hours, poured into ice water and extracted with hexane. The hexane extracts were combined and washed twice with a methanol/water mixture (ratio 6:4) and once with a solution of saturated sodium chloride, dried over sodium sulfate, filtered and evaporated. The crude material was purified by column chromatography on silica gel and elution with ethyl ether/hexane (1:3) to yield ethyl cis and trans-3,7-dimethyl-9-(2,4-dimethyl-5-methoxymethyl-3-thienyl)-2,4,6,8-nonatetraenoate.

EXAMPLE 87

(2,4-dimethyl-3-thenyl)triphenylphosphonium bromide 4.4 G of 2,4-dimethyl-3-hydroxymethylthiophene and 10.7 g. of triphenylphosphonium bromide was dissolved in 40 ml. of acetonitrile and stirred at 40° C. for 1 hour. The resulting solution was cooled and 150 ml. of ethyl ether was added. The white precipitate which formed was filtered and washed with cold acetone to yield (2,4-dimethyl-3-thenyl)triphenylphosphonium bromide, m.p. 262°–265° C.

EXAMPLE 88

Ethyl all trans-3,7-dimethyl-9-(2,4-dimethyl-3-thienyl)-2,4,6,8-nonatetraenoate 1.35 G. of a 50% suspension of sodium hydride in mineral oil was washed once with hexane and suspended in 120 ml. of dimethylformamide. At 0° C., 12.0 g of a suspension of (2,4-dimethyl-3-thenyl)triphenylphosphonium bromide in 20 ml. of dimethylformamide was dropped in and stirred for 30 minutes. 5.8 G. of a solution of 3-methyl-7-formyl-octa-2,4,6-trienoic acid ethyl ester in 30 ml. of dimethylformamide then was added dropwise. After stirring at 0° C. for 2 hours, the reaction mixture was poured into ice water and extracted several times with hexane. The combined hexane extracts were washed twice with a methanol/water mixture (ratio 6:4), once with a saturated sodium chloride solution, dried over sodium sulfate, filtered and evaporated. The resulting crude product was purified by column chromatography on silica gel and elution with ethyl ether/hexane (1:4). Recrystallization from hexane yielded ethyl all trans-3,7-dimethyl-9-(2,4-dimethyl-3-thienyl)-2,4,6,8-nonatetraenoate, m.p. 69°–71° C.

EXAMPLE 89

3-bromo-2,4-dimethyl-5-(methylthio)thiophene 20.0 G. of 2,4-dibromo-3,5-dimethylthiophene was dissolved in 300 ml. of anhydrous ethyl ether. The resulting solution was cooled to −70° C. with stirring under argon. 32 Ml. of a 2.4 M solution of n-butyl lithium was added slowly and the solution was warmed to −32° C. for 10 minutes and then cooled again to −70° C. 7.5 G. of dimethyl disulfide was added slowly while the temperature was maintained at −70° C. The resulting solution was warmed to room temperature and stirred for 2 hours then poured into ice water, stirred for 15 minutes, and extracted with ethyl ether. The combined ether extracts were washed with water, 5% sodium carbonate, and saturated sodium chloride solution; dried over sodium sulfate, filtered and evaporated to yield 3-bromo-2,4-dimethyl-5-(methylthio)thiophene.

EXAMPLE 90

2,4-dimethyl-5-(methylthio)thiophene-3-carboxaldehdye 18.5 G. of 3-bromo-2,4-dimethyl-5-(methylthio)thiophene was dissolved in 250 ml. of anhydrous ethyl ether and cooled to −70° C. with stirring under argon. 34 Ml. of a 2.4 M solution of n-butyl lithium was added slowly and the solution was warmed to −25° C. for 10 minutes. The reaction mixture was again cooled to −70° C. and 7.3 g. of dimethylformamide was added slowly. The reaction mixture was stirred at room temperature for 2 hours, poured into ice water, stirred for 15 minutes, and finally extracted with ethyl ether. The combined ether extracts were washed with water, a 5% solution of sodium carbonate, saturated sodium chloride solution, dried over sodium sulfate, filtered, and evaporated to yield 2,4-dimethyl-5-(methylthio)thiophene-3-carboxyaldehyde.

EXAMPLE 91

2,4-dimethyl-3-hydroxymethyl-5-(methylthio)thiophene 15.0 G of 2,4-dimethyl-5-(methylthio)thiophene-3-carboxyldehyde was dissolved in 150 ml. of dry ethanol with stirring at 20° C. 0.8 G. of sodium borohydride was added and the mixture was stirred for 30 minutes, then poured into ice water and extracted with ethyl ether. The combined ether extracts were washed with a solution of 5% sodium carbonate and saturated sodium chloride solution, dried over sodium sulfate, filtered, and evaporated to yield 2,4-dimethyl-3-hydroxymethyl-5-(methylthio)thiophene.

EXAMPLE 92

[2,4-dimethyl-5-(methylthio)-3-thenyl]triphenylphosphonium bromide 14.0 G. of 2,4-dimethyl-3-hydroxymethyl-5-(methylthio)thiophene and 26.0 G. of triphenylphosphonium bromide were dissolved in 75 ml. of acetonitrile and stirred at 40° C. for 1 hour. The resulting mixture was cooled and poured into 150 ml. of ethyl acetate then treated with ethyl ether/hexane (5:1). The resulting solution was decanted from a gum-like residue. The residue was treated with hot acetone and the resulting white crystals were filtered, washed with cold acetone and dried under high vacuum at 80° C. to yield [2,4-dimethyl-5-(methylthio)-3-thenyl]triphenylphosphonium bromide, m.p. 245°–248° C.

EXAMPLE 93

Ethyl all trans-3,7-dimethyl-9-[2,4-dimethyl-5-(methylthio)-3-thienyl]-2,4,6,8-nonatetraenoate 1.40 G. of a 50% suspension of sodium hydride in mineral oil was washed once with pentane and suspended in 120 ml. of dimethylformamide. At 0° C., 14.5 g. of a suspension of [2,4-dimethyl-5-(methylthio)-3-thenyl]triphenylphosphonium bromide in 30 ml. of dimethylformamide was added dropwise and stirred for 30 minutes. 6.5 G. of a solution of 3-methyl-7-formyl-octa-2,4,6-trienoic acid ethyl ester in 30 ml. of dimethylformamide was then added dropwise. After stirring at 0° C. for 2 hours, the reaction mixture was poured into ice water and extracted several times with hexane. The combined hexane extracts were washed twice with methanol/water (6:4), once with a solution of saturated sodium chloride, dried over sodium sulfate, filtered, and evaporated. The resulting crude product was purified by column chromatography on silica gel and elution with ethyl ether/hexane (1:4). Recrystallization from ethyl ether/hexane (1:9) yielded ethyl all trans-3,7-dimethyl-9-[2,4-dimethyl-5-(methylthio)-3-thienyl]-2,4,6,8-nonatetraenoate, m.p. 76°–78° C.

EXAMPLE 94

Ethyl 3,7-dimethyl-9-(3-methyl-5-nitro-2-thienyl)-2,4,6,8-nonatetraenoate 3.7 G. of a 50% suspension of sodium hydride in mineral oil was washed once with pentane, and suspended in 450 ml. of dimethylformamide. At 0° C., 42.8 g. of a solution of triphenyl-(7-ethoxycarbonyl-2,6-dimethyl-2,4,6-heptatrienyl)-phosphonium bromide in 200 ml. of dimethylformamide was added slowly and stirred for 45 minutes. This reaction mixture was added slowly to a cold (0° C.) solution of 3-methyl-5-nitrothiophene-2-carboxaldehyde in 350 ml. of dimethylformamide under argon. The reaction mixture then was stirred at 5° C. for 2 hours, poured into ice water and extracted with ethyl ether. The ether extracts were combined, washed twice with water, dried over sodium sulfate, filtered and evaporated. The resulting crude solid was dissolved in 600 ml. of ethyl acetate and diluted with 4 liters of hexane. This was washed three times with a water/methanol mixture (ratio 4:6) and the washings were extracted twice with hexane. All organic extracts were combined, washed once with a water/methanol mixture (ratio 4:6), once with a solution of saturated sodium chloride, dried over sodium sulfate, filtered and evaporated to yield ethyl cis and trans-3,7-dimethyl-9-(3-methyl-5-nitro-2-thienyl)-2,4,6,8-nonatetraenoate.

EXAMPLE 95

2,4-diethyl-5-methyl-thiophene 18.2 G. of 2,4-diacetyl-5-methyl-thiophene and 40 ml. of hydrazine (95%+) were dissolved in 160 ml. of diethylene glycol. The resulting solution was heated to the reflux for 1 hour during which 4.0 ml. of distillate was collected. 50 Ml. of diethylene glycol then was added and after refluxing and additional hour, 4.0 ml. more of distillate was collected. The reaction mixture was then refluxed at 160° C. for 2.5 hours, and cooled to below 80° C. 50 G. of potassium hydroxide then was added with stirring and the resulting mixture was carefully warmed to 120° C. heated to reflux for 20 minutes and finally distilled until no further distillate was collected at 210° C. The resulting distillate was cooled and poured into 500 ml. of ice cold 2 N hydrochloric acid. The resulting product was extracted several times with diethyl ether. The combined organic phases were washed with water, sodium bicarbonate solution and water, dried over sodium sulfate, filtered and evaporated. The resulting crude product was purified by distillation to yield 2,4-diethyl-5-emthyl-thiophene, m.p. 85°–87° C. (20 mm).

EXAMPLE 96

2,4-diethyl-5-methyl-3-chloromethylthiophene 15.0 G. of 2,4-diethyl-5-methylethiophene, 65 ml. of acetic acid, 130 ml. of 12 N hydrochloric acid and 8.9 g. of formaldehyde (37% solution) were heated at 70° C. for 2.5 hours. The resulting reaction mixture was cooled, poured into 600 ml. of water and extracted several times with diethyl ether. The combined organic phases were washed with water, sodium bicarbonate solution and water, dried over sodium sulfate, filtered and evaporated to yield 2,4-diethyl-5-methyl-3-chloromethylthiophene.

EXAMPLE 97

(2,4-diethyl-5-methyl-3-thenyl)triphenylphosphonium chloride 19.7 G. of 2,4-diethyl-5-methyl-3-chloromethylthiophene and 39.5 g. of triphenylphosphine were dissolved in 400 ml. of toluene. The resulting solution was heated at 115° C. overnight under argon and then cooled to room temperature. The white phosphonium salt which precipitated was collected by filtration, washed with toluene and dried at 100° C. under high vacuum to yield (2,4-diethyl-5-methyl-3-thenyl)triphenylphosphonium chloride, m.p. 192°–194° C.

EXAMPLE 98

All trans-3,7-dimethyl-9-(2,4-diethyl-5-methyl-3-thienyl)-2,4,6,8-nonatetraenoic acid ethyl ester 27.0 G. of (2,4-diethyl-5-methyl-3-thenyl)triphenyl phosphonium chloride was suspended in 400 ml. of butylene oxide and 13.3 g. of 3-methyl-7-formyl-octa-2,4,6-trienoic acid ethyl ester were added. The resulting mixture was refluxed under argon for 3 hours after which the solvent was evaporated. The resulting residue was diluted with a mixture of methanol/water (6:4) and extracted several times with hexane. The combined organic phases were washed once with methanol/water (6:4), dried over sodium sulfate, filtered and evaporated. The resulting crude product was purified by column chromatography (hexane/5% ethyl acetate). Two recrystallizations from hexane yielded all trans-3,7-dimethyl-9-(2,4-diethyl-5-methyl-3-thienyl)-2,4,6,8-nonatetraenoic acid ethyl ester, m.p. 79°–80° C.

EXAMPLE 99

(3-thenyl)triphenylphosphonium bromide 34.3 G. of 3-bromomethyl-thiophene and 61.0 g. of triphenylphosphine were dissolved in 500 ml. of benzene. The resulting mixture was refluxed overnight under argon and then cooled to room temperature. The tan phosphonium salt which precipitated was collected by filtration, washed several times with toluene and dried at 100° C. under high vacuum to yield (3-thenyl)-triphenylphosphonium bromide, m.p. >270° C.

EXAMPLE 100

2,4,6-trans-8-cis-3,7-dimethyl-9-(3-thienyl)-2,4,6,8-nonatetraenoic acid ethyl ester 22.5 G. of (3-thenyl)triphenylphosphonium bromide was suspended in 200 ml. dimethylformamide and cooled to 0°–5° C. 2.4 G. of a 50% suspension of sodium hydride in mineral oil was added in portions. After stirring for 30 minutes, a solution of 11.4 g. of 3-methyl-7-formyl-octa-2,4,6-trienoic acid ethyl ester in 45 ml. of dimethylformamide was added dropwise. After stirring for 3 hours at 0°–5° C., the reaction mixture was poured into 1000 ml. of water and extracted several times with ethyl acetate. The combined organic phases were washed twice with water, dried over sodium sulfate, filtered and evaporated. The resulting crude product was purified by column chromatography (hexane/10% ethyl acetate). Recrystallizations from hexane/15% ethyl acetate and hexane yielded 2,4,6-trans-8-cis-3,7-dimethyl-9-(3-thienyl)-2,4,6,8-nonatetraenoic acid ethyl ester, m.p. 59.5°–60° C.

EXAMPLE 101

All trans-3,7-dimethyl-9-(3-thienyl)-2,4,6,8-nonatetraenoic acid ethyl ester 26.6 G. of (3-thenyl)triphenylphosphonium bromide was suspended in 200 ml. of dimethylformamide and the mixture was cooled to 0°–5° C. 2.90 G. of a 50% suspension of sodium hydride in mineral oil was added in portions. After stirring for 1 hour, a solution of 13.7 g. of 3-methyl-7-formyl-octa-2,4,6-trienoic acid ethyl ester was added dropwise. After stirring for 2 hours at 0°–5° C., the reaction mixture was poured into 1000 ml. of water and extracted several times with ethyl acetate. The combined organic phases were washed twice with water, dried over sodium sulfate, filtered and evaporated. The resulting crude product was purified by column chromatography (hexane/25% ethyl acetate). Recrystallization once from hexane/25% ethyl acetate and repeatedly from hexane/ether yielded all trans-3,7-dimethyl-9-(3-thienyl)-2,4,6,8-nonatetraenoic acid ethyl ester, m.p. 99°–101° C.

EXAMPLE 102

3-chloromethyl-2,5-dichloro-4-methylthiophene

A mixture of 61.59 g. (0.368 mol) of 2,5-dichloro-3-methylthiophene, 13.1 g. of paraformaldehyde and 3.1 g. of zinc chloride was heated to 55° C. Hydrogen chloride gas was passed through the mixture for 7.25 hours. The resulting mixture was cooled and poured into a mixture of ether and ice water. The organic phase was separated and washed with sodium chloride solution, sodium bicarbonate solution and sodium chloride solution again. Evaporation of the dried solvent gave a dark brown oil which was distilled under reduced pressure to yield 3-chloromethyl-2,5-dichloro-4-methylthiophene as a pale yellow liquid, b.p. 87°–92° C./0.75 mm.

EXAMPLE 103

(2,5-dichloro-4-methyl-3-thenyl)triphenylphosphonium chloride

A mixture of 25.4 g. (0.12 mol) of 3-chloromethyl-2,5-dichloro-4-methylthiophene, 34.6 g. (0.132 mol) of triphenylphosphine and 200 ml. of benzene was heated to the reflux overnight. The resulting beige solid was filtered to yield (2,5-dichloro-4-methyl-3-thenyl)-triphenylphosphonium chloride, m.p. 238°–240° C.

EXAMPLE 104

Ethyl all trans-3,7-dimethyl-9-(2,5-dichloro-4-methyl-3-thienyl)-nona-2,4,6,8-tetraenoate 12.3 Ml. of n-butyl lithium (2.45 M in hexane) was added slowly to a cold (−10° C.) suspension of 14.6 g. (30.1 mmol) of (2,5-dichloro-4-methyl-3-thenyl)triphenylphosphonium chloride in 200 ml. of ether. The resulting reaction mixture was stirred for 10 minutes. A solution of 6.27 g. (30.1 mmol) of 3-methyl-7-formylocta-2,4,6-trienoic acid ethyl ester in 100 ml. of ether then was added at −10° C. The reaction mixture was allowed to warm slowly to room temperature over a 2-hour period then was poured into ice water and extracted with ether. The ether extracts were washed with saturated sodium chloride solution, dried with sodium sulfate and evaporated to yield a yellow oil which was triturated several times with hexane and filtered. The hexane extracts were concentrated and the resulting residue was purified by chromatography on silica gel. Elution with hexane containing 1% ether yielded a yellow oil which crystallized. Repeated crystallization from pentane yielded ethyl all trans-3,7-dimethyl-9-(2,5-dichloro-4-methyl-3-thienyl)-nona-2,4,6,8-tetraenoate as yellow crystals, m.p. 77°–83° C.

EXAMPLE 105

All trans-3,7-dimethyl-9-(2,4,5-trimethyl-3-thienyl)-2,4,6,8-nonatetraen-1-ol 10.0 G. of all trans-3,7-dimethyl-9-(2,4,5-trimethyl-3-thienyl)-2,4,6,8-nonatetraenoic acid ethyl ester was dissolved in 200 ml. of toluene and cooled to −78° C. Di-isobutylaluminum hydride (55.5 ml. of a 25% solution in hexane) was added slowly to the resulting mixture. After stirring at −78° C. for 30 minutes the reaction mixture was warmed to 0° C. and 200 ml. of 50% aqueous methanol solution was added slowly. The resulting reaction mixture was filtered and the filter cake was washed with diethyl ether. The filtrate was extracted several times with diethyl ether. The combined organic phases were washed twice with water, dried over magnesium sulfate, filtered and evaporated to yield all trans-3,7-dimethyl-9-(2,4,5-trimethyl-3-thienyl)-2,4,6,8-nonatetraen-1-ol.

EXAMPLE 106

All trans-3,7-dimethyl-9-(2,4,5-trimethyl-3-thienyl)-1-methoxy-2,4,6,8-nonatetraene 1.056 G. of a 50% suspension of sodium hydride in mineral oil was suspended in 100 ml. of dimethylformamide. 5.76 G. of all trans-3,7-dimethyl-9-(2,4,5-trimethyl-3-thineyl)-2,4,6,8-nonatetraen-1-ol then was added. The resulting reaction mixture was stirred for 5 minutes and then 3.75 ml. of methyl iodide were added with cooling. After stirring at room temperature for about 20 hours the reaction mixture was poured into 200 ml. of water and extracted several times with ethyl acetate. The combined organic phases were washed with water, dried over magnesium sulfate, filtered and evaporated. The resulting crude product was purified by column chromatography (hexane/25% ethyl acetate). Recrystallization from methanol yielded all trans-3,7-dimethyl-9-(2,4,5-trimethyl-3-thienyl)-1-methoxy-2,4,6,8-nonatetraene, m.p. 93°–94° C.

EXAMPLE 107

All trans-3,7-dimethyl-9-(2,4,5-trimethyl-3-thienyl)-2,4,6,8-nonatetraen-1-al 5.1 G. of all trans-3,7-dimethyl-9-(2,4,5-trimethyl-3-thienyl)-2,4,6,8-nonatetraen-1-ol was dissolved in 100 ml. of methylene chloride, which had been previously purified by passing through a column of neutral alumina, and 26.1 g. of manganese dioxide were added. After stirring for 20 hours at room temperature, the reaction mixture was filtered through Celite and evaporated. The resulting crude product was purified by column chromatography (hexane/25% ethyl acetate). Two recrystallizations from hexane/25% ethyl acetate yields all trans-3,7-dimethyl-9-(2,4,5-trimethyl-3-thienyl)-2,4,6,8-nonatetraen-1-al, m.p. 109°–110° C.

EXAMPLE 108

All trans-3,7-dimethyl-9-(2,4,5-trimethyl-3-thienyl)-2,4,6,8-nonatetraenamide 6.04 G. of all trans-3,7-dimethyl-9-(2,4,5-trimethyl-3-thienyl)-2,4,6,8-nonatetraenoic acid was suspended in 100 ml. of toluene. 3.78 Ml. was dropped into the suspension at room temperature. After stirring for about 20 hours, the acid had dissolved and a red solution of the acid chlorine resulted. The toluene then was evaporated and the acid chloride was dissolved in 150 ml. of anhydrous liquid ammonia. The resulting mixture was stirred at low temperature for 3 hours, and then at room temperature for 18 hours. The resulting reaction mixture was diluted with methylene chloride, poured into water and extracted several times with methylene chloride. The combined organic phases were washed once with saturated sodium chloride solution, dried over magnesium sulfate, filtered and evaporated. Two recrystallizations from 95% ethanol yielded all trans-3,7-dimethyl-9-(2,4,5-trimethyl-3-thienyl)-2,4,6,8-nonatetraenamide, m.p. 198°–2°–3° C.

We claim:
1. A compound represented by the formula

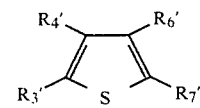

wherein one of $R'_6$ or $R'_7$ is

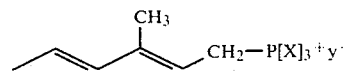

and the other of R'$_6$ or R'$_7$ and R'$_3$ and R'$_4$ are hydrogen, lower alkyl thio, lower alkoxy-lower alkyl, hydroxy methyl, halogen, lower alkyl, lower alkoxy, amino, carboxyl, mono(lower alkyl)amino, di(lower alkyl)amino, mono(lower alkyl)amino lower alkyl, di(lower alkyl)amino lower alkyl, hydroxy, lower alkenyl, lower alkenoxy, lower alkanoyl, lower alkanoyloxy, nitro, lower alkoxycarbonyl or lower alkanoylamido, X is aryl selected from the group consisting of phenyl, lower alkyl-substituted phenyl and lower alkoxysubstituted phenyl, y is an anion of an organic acid or an inorganic acid and all of the lower alkyl, lower alkenyl and lower alkanoyl groups in the above radicals have up to 6 carbon atoms.

2. A compound represented by the formula

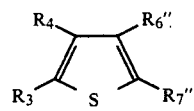

wherein one of R"$_6$ or R"$_7$ is

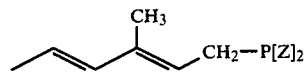

and the other of R"$_6$ or R"$_7$ and R$_3$ and R$_4$ are hydrogen, lower alkyl thio, lower alkoxy-lower alkyl, hydroxymethyl, halogen, lower alkyl, lower alkoxy, amino, carboxyl, mono(lower alkyl)amino, di(lower alkyl)amino, mono(lower alkyl)amino lower alkyl, di(lower alkyl)amino lower alkyl, hydroxy, lower alkenyl, lower alkenoxy, lower alkanoyl, lower alkanoyloxy, nitro, lower alkoxycarbonyl or lower alkanoylamido, Z is lower alkoxy and all of the lower alkyl, lower alkenyl and lower alkanoyl groups in the above radicals have up to 6 carbon atoms.

* * * * *